United States Patent
Tsvelikhovsky

(10) Patent No.: US 10,844,050 B2
(45) Date of Patent: Nov. 24, 2020

(54) CYCLIZATION PROCESSES OF HYDROXYALKENOIC ACIDS AND PRODUCTS THEREOF

(71) Applicant: Yissum Research Development Company, of The Hebrew University of Jerusalem Ltd., Jerusalem (IL)

(72) Inventor: Dmitry Tsvelikhovsky, Nof Hagalil (IL)

(73) Assignee: YISSUM RESEARCH DEVELOPMENT COMPANY OF THE HEBREW UNIVERSITY OF JERUSALEM LTD., Jerusalem (IL)

(*) Notice: Subject to any disclaimer, the term of this patent is extended or adjusted under 35 U.S.C. 154(b) by 0 days.

(21) Appl. No.: 16/485,802

(22) PCT Filed: Feb. 14, 2018

(86) PCT No.: PCT/IL2018/050169
§ 371 (c)(1),
(2) Date: Aug. 14, 2019

(87) PCT Pub. No.: WO2018/150421
PCT Pub. Date: Aug. 23, 2018

(65) Prior Publication Data
US 2020/0048233 A1 Feb. 13, 2020

Related U.S. Application Data

(60) Provisional application No. 62/458,624, filed on Feb. 14, 2017.

(51) Int. Cl.
| | | |
|---|---|---|
| C07D 309/32 | (2006.01) | |
| C07D 409/06 | (2006.01) | |
| C07C 45/45 | (2006.01) | |
| C07C 49/647 | (2006.01) | |
| C07D 307/58 | (2006.01) | |
| C07D 313/04 | (2006.01) | |
| C07D 313/18 | (2006.01) | |
| C07D 407/04 | (2006.01) | |

(52) U.S. Cl.
CPC .......... *C07D 409/06* (2013.01); *C07C 45/455* (2013.01); *C07C 49/647* (2013.01); *C07D 307/58* (2013.01); *C07D 309/32* (2013.01); *C07D 313/04* (2013.01); *C07D 313/18* (2013.01); *C07D 407/04* (2013.01)

(58) Field of Classification Search
CPC .. C07D 409/06; C07D 309/32; C07D 313/18; C07D 307/58; C07D 407/04; C07D 313/04; C07C 45/455; C07C 49/647
USPC ...................................................... 549/273
See application file for complete search history.

(56) References Cited

PUBLICATIONS

Abdelrahman O. A., et al. (2014). Analysis of kinetics and reaction pathways in the aqueous-phase hydrogenation of levulinic acid to form γ-valerolactone over Ru/C. ACS Catalysis 4 (4), 1171-1181.
Arthuis, M., et al. (2011). Synthesis and Structure—Activity Relationships of Constrained Heterocyclic Analogues of Combretastatin A4. ChemMedChem, 6(9), 1693-1705.
Baskaran, S., et al. (1990). A general approach to the synthesis of butanolides: synthesis of the sex pheromone of the Japanese beetle. The Journal of Organic Chemistry, 55(3), 891-895.
Birtwistle, D. H., et al. (1988). Diastereoselectivity in the intramolecular diels-alder reaction of dienylpropynoates. Tetrahedron, 44(23), 7309-7318.
Braun, M., et al. (2006). Tsuji—Trost allylic alkylation with ketone enolates. Angewandte Chemie International Edition, 45(42), 6952-6955.
Chakravarty, M., et al. (2006). Palladium-catalyzed coupling of allenylphosphonates, phenylallenes, and allenyl esters: Remarkable salt effect and routes to novel benzofurans and isocoumarins. The Journal of organic chemistry, 71(24), 9128-9138.
Chang, H. T., et al. (2007). Cobalt-catalyzed reductive coupling of activated alkenes with alkynes. Journal of the American Chemical Society, 129(39), 12032-12041.
Cho, J. H., et al. (2002). Synthesis and MMP-Inhibitory Activity of Gelastatin Analogues. Helvetica chimica acta, 85(11), 3994-3999.
De Rycke, N., et al. (2014). Direct intramolecular catalytic enantioselective alkylation of oxazolidinone bromoalkanoate imides. Synlett, 25(19), 2802-2805; and Supporting Information pp. 1-13, XP055470G48, DOI: 10.1055/S-0034-1379236.

(Continued)

*Primary Examiner* — Taylor V Oh
(74) *Attorney, Agent, or Firm* — Mark S. Cohen; Pearl Cohen Zedek Latzer Baratz LLP

(57) ABSTRACT

The invention provides efficient cyclization processes of hydroxyalkenoic acids and products produced therefrom. The following reactions are claimed: Formula (I), (II), (V) and (VI).

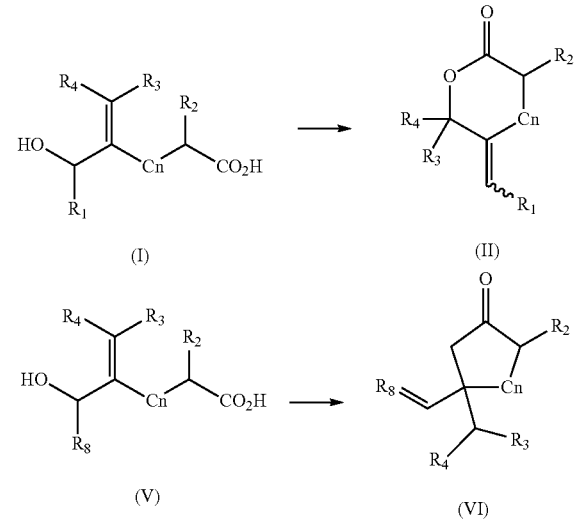

17 Claims, No Drawings

(56) References Cited

PUBLICATIONS

Drewes, S. E., et al. (1992). Synthesis, resolution and assignment of absolute configuration of 2-(α-hydroxy) aryl acrylate esters. Tetrahedron: Asymmetry, 3(2), 255-260.

El-Gamal, A. A., et al. (2005). Xenibellols A and B, New Diterpenoids from the Formosan Soft Coral Xenia u mbellata. Organic letters, 7(10), 2023-2025.

Ferraz, H., et al. (2008). Natural occurrence, biological activities and synthesis of eight-, nine-, and eleven-membered ring lactones. Química Nova, 31(4), 885-900.

Gupta, S. C., et al. (2011). Bharangin, a diterpenoid quinonemethide, abolishes constitutive and inducible nuclear factor-κB (NF-κB) activation by modifying p65 on cysteine 38 residue and reducing inhibitor of nuclear factor-κB α kinase activation, leading to suppression of NF-κB-regulated gene expression and sensitization of tumor cells to chemotherapeutic agents. Molecular pharmacology, 80(5), 769-781.

Hanzawa, Y., et al. (1990). Palladium (0)-mediated intramolecular lactonization of allylic alcohol derivatives; unusual substituent effect of the trifluoromethyl group on δ-lactone formation. Journal of the Chemical Society, Chemical Communications, (5), 394-395.

Harada, K., et al. (2007). An efficient synthesis of the CD rings model for merrilactone A. Tetrahedron letters, 48(35), 6105-6108.

Hargaden, G. C. et al. (2007). The development of the asymmetric Nozaki—Hiyama—Kishi reaction. Advanced Synthesis & Catalysis, 349(16), 2407-2424.

Kinoshita, H., et al. (2004). Water Enables Direct Use of Allyl Alcohol for Tsuji—Trost Reaction without Activators. Organic letters, 6(22), 4085-4088.

Kratochvil, J., et al. (2015). Fully Substituted Pyranones via Quasi-Heterogeneous Genuinely Ligand-Free Migita—Stille Coupling of Iodoacrylates. Organic letters, 17(3), 520-523.

Kurihara, T., et al. (1976). Synthesis of lactones and cycloalkanes. Cyclization of ω-hydroxy acids and ethyl α-cyano-ω-hydroxycarboxylates. Tetrahedron Letters, 17(28), 2455-2458.

Larock, R. C., et al. (1993). Synthesis of unsaturated lactones via palladium-catalyzed cyclization of alkenoic acids. The Journal of Organic Chemistry, 58(20), 5298-5300.

Lee, H. J., et al. (1997). Gelastatins A and B, new inhibitors of gelatinase A from Westerdykella multispora F50733. The Journal of antibiotics, 50(4), 357-359.

Li, P. F., et al. (2014). 1, n-Rearrangement of allylic alcohols promoted by hot water: Application to the synthesis of navenone B, a polyene natural product. The Journal of organic chemistry, 79(9), 3955-3962.

Macahig, R. A., et al. (2010). Secoiridoid and iridoid glucosides from the leaves of Fraxinus griffithii. Journal of natural medicines, 64(1), 1.

Matsuo, K., et al. (2006). The first synthesis of (-)-plakolide A. Heterocycles, 68(7), 1401-1407.

Mazur, Y., et al. (1960). The Synthesis of the Steroidal Sapogenins1, 2. Journal of the American Chemical Society, 82(22), 5889-5908.

Mori, K., et al. (1985). Biochemical preparations of both the enantiomers of methyl 3-hydroxypentanoate and their conversion to the enantiomers of 4-hexanolide, the pheromone of trogoderma glabrum. Tetrahedron, 41(5), 919-925.

Mostinski, Y., et al. (2017). Palladium-Catalyzed Cyclization of Free Hydroxyalkenoic Acids: Regio-and Chemoselective Access to Methylene Lactones. Advanced Synthesis & Catalysis, 359(7), 1164-1169.

Mousouri, E., et al. (2014). Isolation of megaritolactones and other bioactive metabolites from 'megaritiki'table olives and debittering water. Journal of agricultural and food chemistry, 62(3), 660-667.

Ochiai, M., et al. (1985). Iodine (III)-Mediated Intramolecular Cyclization of Hydroxy Allylsilanes: Synthesis of 5-or 6-Membered β-Methylene Cyclic Ethers. Chemical and pharmaceutical bulletin, 33(3), 989-997.

Ortega, A.,et al. (1989). A tris-norsesquiterpene lactone and other sesquiterpenes from Calea crocinervosa. Phytochemistry, 28(10), 2735-2736.

Roomi, M. W., et al. (1970). Some reactions of sterculic and malvalic acids. A new source of malvalic acid. Canadian journal of biochemistry, 48(7), 759-762.

Sengoku, T., et al. (2011). New Synthetic Methodology toward Macrolides/Macrolactams via Palladium-Catalyzed Carbon-Heteroatom Bond-Forming Reactions. Synlett, 2011(12), 1766-1768.

Shiina, I. (2007). Total synthesis of natural 8-and 9-membered lactones: recent advancements in medium-sized ring formation. Chemical reviews, 107(1), 239-273.

Sivák, I., et al. (2016). Chromatography-free stereoselective synthesis of (R)-3-benzylpiperidine. Tetrahedron Letters, 57(10), 1079-1082.

Suzuki, Y., et al. (2015). Intramolecular Tsuji—Trost-type Allylation of Carboxylic Acids: Asymmetric Synthesis of Highly π-Allyl Donative Lactones. Journal of the American Chemical Society, 137(30), 9539-9542.

Taylor, R. E., et al. (1999). 2-Bromoallyl Acetate: A Useful Structural Unit for Sequential Carbon—Carbon Bond Formation. Organic Letters, 1(3), 467-470.

Thompson, C. M., et al. (2009). Total synthesis and cytoprotective properties of dykellic acid. Journal of medicinal chemistry, 52(1), 117-125.

Trend, R. M., et al. (2003). Palladium-catalyzed oxidative Wacker cyclizations in nonpolar organic solvents with molecular oxygen: a stepping stone to asymmetric aerobic cyclizations. Angewandte Chemie International Edition, 42(25), 2892-2895.

Trost, B. M. (1989). Cyclizations via Palladium-Catalyzed Allylic Alkylations [New Synthetic Methods (79)]. Angewandte Chemie International Edition in English, 28(9), 1173-1192.

Trost, B. M., et al. (1973). New synthetic reactions. Asymmetric induction in allylic alkylations. Journal of the American Chemical Society, 95(24), 8200-8201.

Trost, B. M., et al. (1986). A total synthesis of plumericin, allamcin and allamandin. Part 2. A biomimetic strategy. Journal of the American Chemical Society, 108(16), 4974-4983.

Tsuji, J. A. (2004). Palladium reagents and catalysts: New perspectives for the 21st century.

Wang, Y. H., et al. (2010). Diastereoselective γ-vinyl butyrolactone synthesis via gold catalyzed cyclization of allylic acetate. Chemical Communications, 46(4), 577-579.

Yet, L. (2000). Metal-mediated synthesis of medium-sized rings. Chemical reviews, 100(8), 2963-3008.

CYCLIZATION PROCESSES OF HYDROXYALKENOIC ACIDS AND PRODUCTS THEREOF

CROSS-REFERENCE TO RELATED APPLICATIONS

This application is a National Phase Application of PCT International Application No. PCT/IL2018/050169, International Filing Date Feb. 14, 2018, claiming the benefit of U.S. patent application Ser. No. 62/458,624, filed Feb. 14, 2017 which are hereby incorporated by reference.

TECHNOLOGICAL FIELD

The present invention is in the field of cyclization processes of hydroxyalkenoic acids and products produced therefrom.

BACKGROUND ART

References considered to be relevant as background to the presently disclosed subject matter are listed below:
[1] S. Baskaran, Imadul Islam, S. Chandrasekaran, *J. Org. Chem.* 1990, 55, 891-895.
[2] A. A. H. El-Gamal, S. K. Wang, C. Y. Duh, *Org. Lett.* 2005, 7, 2023-2025.
[3] S. C. Gupta, R. Kannappan, J. Kim, G. M. Rahman, S. K. Francis, R. Raveendran, M. S. Nair, J. Das, B. B. Aggarwal, *Mol. Pharmacol.* 2011, 80, 769-81.
[4] K. Harada, H. Ito, H. Hioki, Y. Fukuyama, *Tetrahedron Lett.* 2007, 48, 6105-6108.
[5] R. A. Macahig, L. Harinantenaina, K. Matsunami, H. Otsuka, Y. Takeda, T. Shinzato, *J. Nat. Med.* 2010, 64, 1-8.
[6] E. Mousouri, E. Melliou, P. Magiatis, *J. Agric. Food Chem.* 2014, 62, 660-667.
[7] B. M. Trost, J. M. Balkovec, M. K. T. Mao, *J. Am. Chem. Soc.* 1986, 4974-4983.
[8] H. Lee, M. Chung, C. Lee, B. Yun, H. Chun, Y. Kho, *J. Antibiot.* (Tokyo). 1996, 50, 357-359.
[9] A. Ortega, J. D. E. L. C. Lopez, E. Maldonado, I. De Quimtca, U. Nactonal, A. De Mixtco, C. Extertor, C. Umversitana, *Phytochemistry* 1989, 28, 2735-2736.
[10] C. M. Thompson, C. A. Quinn, P. J. Hergenrother, *J. Med. Chem.* 2009, 52, 117-125.
[11] M. Braun, T. Meier, *Angew. Chemie—Int. Ed.* 2006, 45, 6952-6955.
[12] J. Tsuji, *Palladium Reagents and Catalysts*, 2004.
[13] B. Trost, T. Dietsch, *J. Am. Chem. Soc.* 1973, 95, 8200-8201.
[14] B. M. Trost, *Angew. Chem. Int. Ed. Engl.* 1989, 28, 1173-1192.
[15] H. Kinoshita, H. Shinokubo, K. Oshima, *Org. Lett.* 2004, 6, 4085-4088.
[16] Y. Hanzawa, S. Ishizawa, H. Ito, Y. Kobayashi, T. Taguchi, *J. Chem. Soc. Chem. Commun.* 1990, 5, 394-395.
[17] T. Sengoku, T. Hamamatsu, T. Inuzuka, M. Takahashi, M. Science, F. Engineering, *Synlett* 2011, 12, 1766-1768.
[18] Y. Suzuki, T. Seki, S. Tanaka, M. Kitamura, *J. Am. Chem. Soc.* 2015, 137, 9539-9542.
[19] S. Y. Ko, E. Oh, J. C. Park, J. U. Yoo, *Helv. Chim. Acta* 2002, 85, 3994-3999.
[20] H. T. Chang, T. J. Thiruvellore, C. C. Wang, C. H. Cheng, *J. Am. Chem. Soc.* 2007, 129, 12032-12041.
[21] M. Chakravarty, K. C. K. Swamy, *J. Org. Chem.* 2006, 71, 9128-9138.
[22] M. Arthuis, R. Pontikis, G. G. Chabot, J. Seguin, L. Quentin, S. Bourg, L. Morin-Allory, J. C. Florent, *ChemMedChem* 2011, 6, 1693-1705.
[23] J. Kratochvíl, Z. Novák, M. Ghavre, L. Nováková, A. Růžička, J. Kuneš, M. Pour, *Org. Lett.* 2015, 17, 520-523.
[24] P. J. Guiry, *Adv. Synth. Catal.* 2007, 349, 2407-2424.
[25] R. E. Taylor, J. P. Ciavarri, *Org. Lett.* 1999, 1, 467-469.
[26] O. A. Abdelrahman, A. Heyden, J. Q. Bond, *ACS Catal.* 2014, 4, 1171-1181.
[27] K. Mori, *Tetrahedron* 1985, 41, 919-925.
[28] Y. Mazur, N. Danieli, F. Sondheimer, *J. Am. Chem. Soc.* 1960, 82, 5889-5908.
[29] L. Yet, *Chem. Rev.* 2000, 100, 2963-3007.
[30] T. Kurihara, Y. Nakajima, O. Mitsunobu, *Tetrahedron Lett.* 1976, 17, 2455-2458.
[31] H. M. C. Ferraz, F. I. Bombonato, M. K. Sano, L. S. Longo, *Quim. Nova* 2008, 31, 885-900.
[32] I. Shiina, *Chem. Rev.* 2007, 107, 239-273.
[33] R. C. Larock, T. R. Hightower, *J. Org. Chem.* 1993, 58, 5298-5300.
[34] R. M. Trend, Y. K. Ramtohul, E. M. Ferreira, B. M. Stoltz, *Angew. Chemie—Int. Ed.* 2003, 42, 2892-2895.
[35] P. F. Li, H. L. Wang, J. Qu, *J. Org. Chem.* 2014, 79, 3955-3962.
[36] D. H. Birtwistle, J. M. Brown, M. W. Foxton, *Tetrahedron* 1988, 44, 7309-7318.

Acknowledgement of the above references herein is not to be inferred as meaning that these are in any way relevant to the patentability of the presently disclosed subject matter.

BACKGROUND

Medium-sized methylene lactone structures are frequently observed as scaffold segments of various biochemical compounds. These architectures have been identified as building blocks of numerous terpenoids, as well as other families of diverse and often remotely related metabolites. [1-7] Typical examples of natural products bearing methylene lactone core, such as Gelastatine, Dykellic acid, and Crocinervolide (Scheme 1), [8-10] a remarkable overlap in their structures becomes apparent.

Scheme 1 - Products from diverse biological origins share methylene lactone scaffold

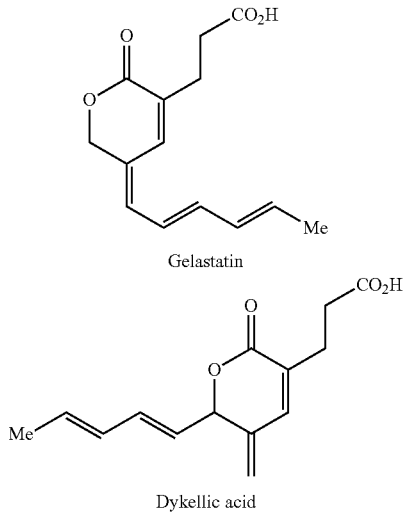

Gelastatin

Dykellic acid

-continued

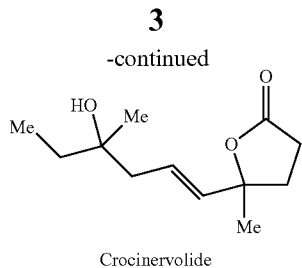

Crocinervolide

The inventors of the present application have found that hydroxyalkenoic acid scaffold can serve as operational, collective key precursor for the construction of such terpenoids having diverse, medium-sized methylene lactone architectures, via regio- and stereo-selecting controlled intramolecular cyclizations. Thus, the present invention provides a streamlined, synthetic methodology allowing for rapid, collective preparation of multiple methylene lactone derivatives, using a common precursor.

General Description

The present invention provides a process for the preparation of compound (II) comprising the step of:

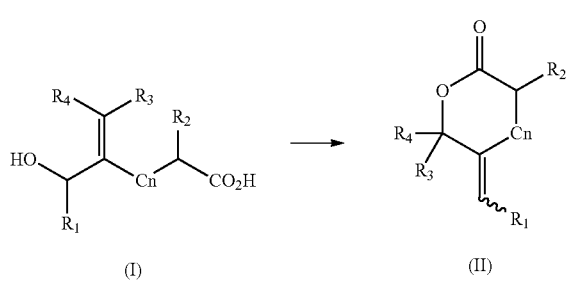

Reacting compound of formula (I) in the presence of at least one Pd catalyst and at least one base; wherein $R_1$ and $R_2$ are each independently selected from a group consisting of H, straight or branched $C_1$-$C_{15}$ alkyl, straight or branched $C_2$-$C_{15}$ alkenyl, straight or branched $C_2$-$C_{15}$ alkynyl, $C_5$-$C_{12}$ aryl, $C_5$-$C_{12}$ heteroaryl; $C_3$-$C_{12}$ cycloalkyl, $C_3$-$C_{12}$ heterocycloalkyl; each optionally substituted by at least one OH, amine, amide, halide, straight or branched $C_1$-$C_{15}$ alkyl, straight or branched $C_2$-$C_{15}$ alkenyl, straight or branched $C_2$-$C_{15}$ alkynyl, —O($C_1$-$C_8$ akyl), —OC(=O)($C_1$-$C_8$ alkyl), —C(=O)($C_1$-$C_8$ alkyl), —C(=O)O($C_1$-$C_8$ alkyl); $C_5$-$C_{12}$ aryl, $C_5$-$C_{12}$ heteroaryl, $C_3$-$C_{12}$ cycloalkyl, $C_3$-$C_{12}$ heterocycloalkyl; $R_3$ and $R_4$ are H; and n is an integer being 1-6.

In a further aspect the invention provides a process for the preparation of compound (IV) comprising the step of:

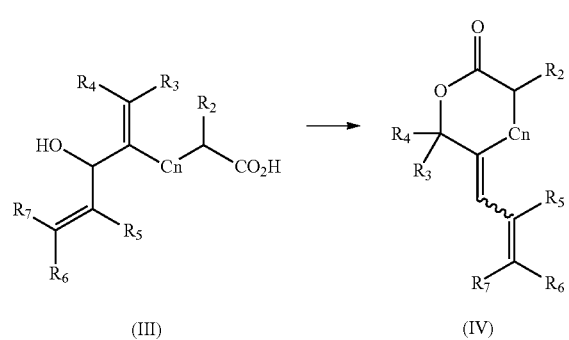

reacting compound of formula (III) in the presence of at least one Pd catalyst and at least one base; wherein $R_2$-$R_7$ are each independently selected from a group consisting of H, straight or branched $C_1$-$C_{15}$ alkyl, straight or branched $C_2$-$C_{15}$ alkenyl, straight or branched $C_2$-$C_{15}$ alkynyl, $C_5$-$C_{12}$ aryl, $C_5$-$C_{12}$ heteroaryl; $C_3$-$C_{12}$ cycloalkyl, $C_3$-$C_{12}$ heterocycloalkyl; each optionally substituted by at least one OH, amine, amide, halide, straight or branched $C_1$-$C_{15}$ alkyl, straight or branched $C_2$-$C_{15}$ alkenyl, straight or branched $C_2$-$C_{15}$ alkynyl, —O($C_1$-$C_8$ akyl), —OC(=O)($C_1$-$C_8$ alkyl), —C(=O)($C_1$-$C_8$ alkyl), —C(=O)O($C_1$-$C_8$ alkyl); $C_5$-$C_{12}$ aryl, $C_5$-$C_{12}$ heteroaryl, $C_3$-$C_{12}$ cycloalkyl, $C_3$-$C_{12}$ heterocycloalkyl; $R_3$ and $R_4$ are H; and n is an integer being 1-6; or $R_5$ and $R_6$ or $R_6$ and $R_7$ or $R_5$ and $R_7$ together with the two carbon atoms they are attached to form a 5 to 15 ring. In some embodiments, said ring is a cycloalkene ring.

In some embodiments, $R_1$ is selected from $C_5$-$C_{12}$ aryl or $C_5$-$C_{12}$ heteroaryl, optionally substituted by at least one OH, amine, amide, halide, straight or branched $C_1$-$C_{15}$ alkyl, straight or branched $C_2$-$C_{15}$ alkenyl, straight or branched $C_2$-$C_{15}$ alkynyl, —O($C_1$-$C_8$ akyl), —OC(=O)($C_1$-$C_8$ alkyl), —C(=O)($C_1$-$C_8$ alkyl), —C(=O)O($C_1$-$C_8$ alkyl); $C_5$-$C_{12}$ aryl, $C_5$-$C_{12}$ heteroaryl.

In other embodiments, $R_1$ is selected from straight or branched $C_1$-$C_{15}$ alkyl, straight or branched $C_2$-$C_{15}$ alkenyl, straight or branched $C_2$-$C_{15}$ alkynyl, optionally substituted by at least one OH, amine, amide, halide, —O($C_1$-$C_8$ akyl), —OC(=O)($C_1$-$C_8$ alkyl), —C(=O)($C_1$-$C_8$ alkyl), —C(=O)O($C_1$-$C_5$ alkyl); $C_5$-$C_{12}$ aryl, $C_5$-$C_{12}$ heteroaryl, $C_3$-$C_{12}$ cycloalkyl, $C_3$-$C_{12}$ heterocycloalkyl.

In further embodiments, $R_2$ is H.

In some embodiments of the process defined above, said compound of formula (III) comprises $R_5$ and $R_6$ or $R_6$ and $R_7$ or $R_5$ and $R_7$ together with the two carbon atoms they are attached to form a 5 to 15 ring. In some embodiments, said ring is a cycloalkene ring. In other embodiments, said ring is a hetero-cycloalkene ring. In further embodiments, said ring is an aromatic ring. In other embodiments, said ring is a herero-aromatic ring.

In some embodiments, said at least one Pd catalyst is selected from Pd(PPh$_3$)$_4$, Pd$_2$(dba)$_3$, Pd(OAc)$_2$, PdCl$_2$, Pd(acac)$_2$ and any combinations thereof.

In further embodiments, said at least one base is selected from K$_2$PO$_4$, Cs$_2$CO$_3$, K$_2$CO$_3$, NaOAc and any combinations thereof.

In some embodiments, a process of the invention is being performed in the presence of at least one organic solvent. In some embodiments, said at least one organic solvent is toluene, THF, DCE, dioxane, CH$_3$CN, toluene, benzene, 1,4-dioxane and any combinations thereof.

In some embodiments, a process of the invention is being performed in a temperature of between 50° C. to 100° C.

A process for the preparation of compound (VI) comprising the step:

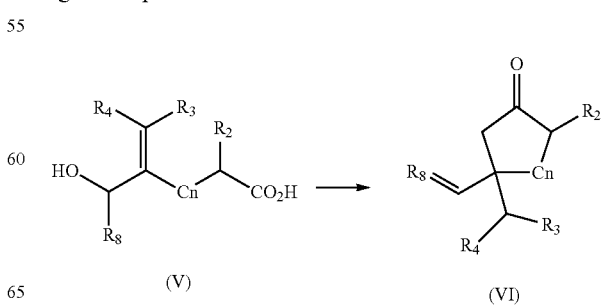

reacting compound of formula (V) in the presence of at least one Pd catalyst and at least one base; wherein $R_2$ is selected from a group consisting of H, straight or branched $C_1$-$C_{15}$ alkyl, straight or branched $C_2$-$C_{15}$ alkenyl, straight or branched $C_2$-$C_{15}$ alkynyl, $C_5$-$C_{12}$ aryl, $C_5$-$C_{12}$ heteroaryl; $C_3$-$C_{12}$ cycloalkyl, $C_3$-$C_{12}$ heterocycloalkyl; each optionally substituted by at least one OH, amine, amide, halide, straight or branched $C_1$-$C_{15}$ alkyl, straight or branched $C_2$-$C_{15}$ alkenyl, straight or branched $C_2$-$C_{15}$ alkynyl, —O($C_1$-$C_8$ akyl), —OC(=O)($C_1$-$C_8$ alkyl), —C(=O)($C_1$-$C_8$ alkyl), —C(=O)O($C_1$-$C_8$ alkyl); $C_5$-$C_{12}$ aryl, $C_5$-$C_{12}$ heteroaryl, $C_3$-$C_{12}$ cycloalkyl, $C_3$-$C_{12}$ heterocloalkyl; $R_3$ and $R_4$ are H;

$R_8$ is straight or branched $C_1$-$C_{15}$ alkyl, straight or branched $C_2$-$C_{15}$ alkenyl, straight or branched $C_2$-$C_{15}$ alkynyl, each optionally substituted by at least one OH, amine, amide, halide, straight or branched $C_1$-$C_{15}$ alkyl, straight or branched $C_2$-$C_{15}$ alkenyl, straight or branched $C_2$-$C_{15}$ alkynyl, —O($C_1$-$C_8$ akyl), —OC(=O)($C_1$-$C_8$ alkyl), —C(=O)($C_1$-$C_8$ alkyl), —C(=O)O($C_1$-$C_8$ alkyl); $C_5$-$C_{12}$ aryl, $C_5$-$C_{12}$ heteroaryl, $C_3$-$C_{12}$ cycloalkyl, $C_3$-$C_{12}$ heterocloalkyl;

and n is an integer being 1-6.

A process for the preparation of compound (I), comprising the step of:

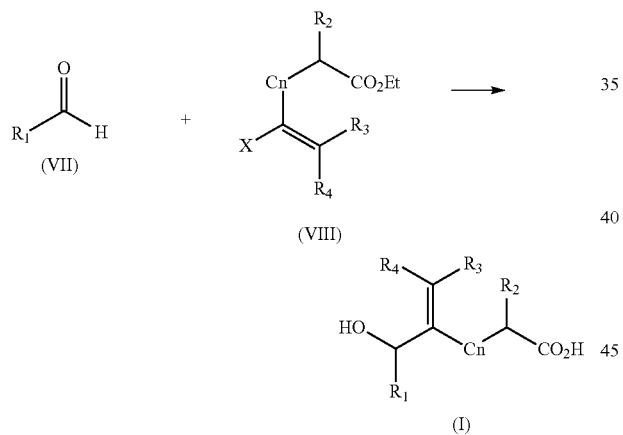

reacting a compound of formula (VII) with a compound of formula (VIII); wherein R1-R4 are as defined herein above.

A process for the preparation of compound (I), comprising the step of:

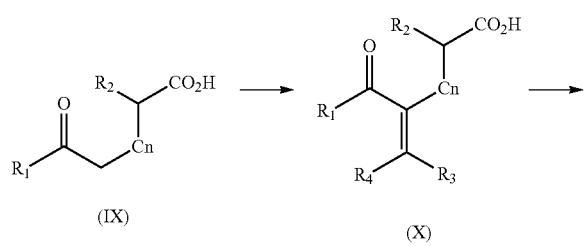

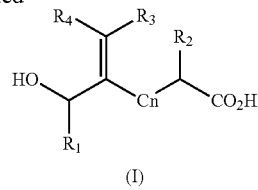

reacting a compound of formula (IX) with a compound of formula (X); wherein R1-R4 are as defined herein above.

It is to be understood that the compounds provided herein may contain one or more chiral centers. Such chiral centers may be of either the (R) or (S) configuration, or may be a mixture thereof. Thus, the compounds provided herein may be enantiomerically pure, or be stereoisomeric or diastereomeric mixtures. In the case where compounds contain a double bond substituted with two or more substituents that are different from H, the configuration of the compound may be either (E) or (Z).

As used herein, "aryl" or "aromatic moiety" or "aromatic ring" that are used interchangeably in this document refers to aromatic monocyclic or multicyclic (either fused or conjugated) groups containing from 5 to 15 carbon atoms. Aryl groups include, but are not limited to groups such as unsubstituted or substituted fluorenyl, unsubstituted or substituted phenyl, and unsubstituted or substituted naphthyl.

As used herein, "heteroaryl" or "hetero-aromatic moiety" or "hetero-aromatic ring" that are used interchangeably in this document refers to a monocyclic or multicyclic (either fused or conjugated) aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl and isoquinolinyl.

The term "cycloalkene ring" or "cycloalkene moiety" that are used interchangeably in this document refers to a monocyclic or multicyclic (either fused or conjugated) groups containing from 5 to 15 carbon atoms that comprises at least one double bond, i.e. at least the double bond connecting the carbon atom connected to R5 and the carbon atom connected to R6.

The term "hetero-cycloalkene ring" or "cycloalkene moiety" that are used interchangeably in this document refers to a monocyclic or multicyclic (either fused or conjugated) groups containing from 5 to 15 carbon atoms that comprises at least one double bond, where one or more, in one embodiment 1 to 3, of the atoms in the ring system is a heteroatom, that is, an element other than carbon, including but not limited to, nitrogen, oxygen or sulfur.

The term "aliphatic moiety" as used herein includes the terms:

"alkyl" (straight, branched chain hydrocarbon having from 1 to 20 carbon atoms) "cyclo-alkyl" (cyclic hydrocar bon, either fused or conjugated, having from 3 to 20 carbon atoms)

"heteroalkyl" (straight, branched chain hydrocarbon having from 1 to 20 carbon atoms, where one or more, in one embodiment 1 to 3, of the atoms in the ring system is a heteroatom, that is, an element other than carbon, including but not limited to, nitrogen, oxygen or sulfur);

"hetero cycloalykl" (cyclic hydrocarbon, either fused or conjugated, having from 3 to 20 carbon atoms where one or more, in one embodiment 1 to 3, of the atoms in the ring system is a heteroatom, that is, an element other than carbon, including but not limited to, nitrogen, oxygen or sulfur);

"alkenyl" (straight, branched chain hydrocarbon having from 2 to 20 carbon atoms comprising at least one double bond, which is not the double bond connecting the carbon atom connected to R5 and the carbon atom connected to R6), "cyclo-alkenyl" (cyclic hydrocarbon having from 3 to 20 carbon atoms comprising at least one double bond, which is not the double bond connecting the carbon atom connected to R5 and the carbon atom connected to $R_6$);

"hetero-alkenyl" (straight, branched chain hydrocarbon having from 2 to 20 carbon atoms comprising at least one double bond, which is not the double bond connecting the carbon atom connected to R5 and the carbon atom connected to R6, where one or more, in one embodiment 1 to 3, of the atoms in the ring system is a heteroatom, that is, an element other than carbon, including but not limited to, nitrogen, oxygen or sulfur);

"hetero cyclo-alkenyl" (cyclic hydrocarbon having from 3 to 20 carbon atoms comprising at least one double bond, which is not the double bond connecting the carbon atom connected to R5 and the carbon atom connected to R6, where one or more, in one embodiment 1 to 3, of the atoms in the ring system is a heteroatom, that is, an element other than carbon, including but not limited to, nitrogen, oxygen or sulfur).

DETAILED DESCRIPTION OF EMBODIMENTS

The spontaneous condensation of hydroxyalkenoic acid 1, generating methylene lactone of Type-2 is well known. [11-14] Inevitably, to obtain methylene (n)-lactone 4, the condensation pathway has to be suppressed. The inventors have found that a necessary diversion of the reaction pathway can take place under Pd(0) Tsuji-Trost conditions via intermediate 3 (as shown in Scheme 2).

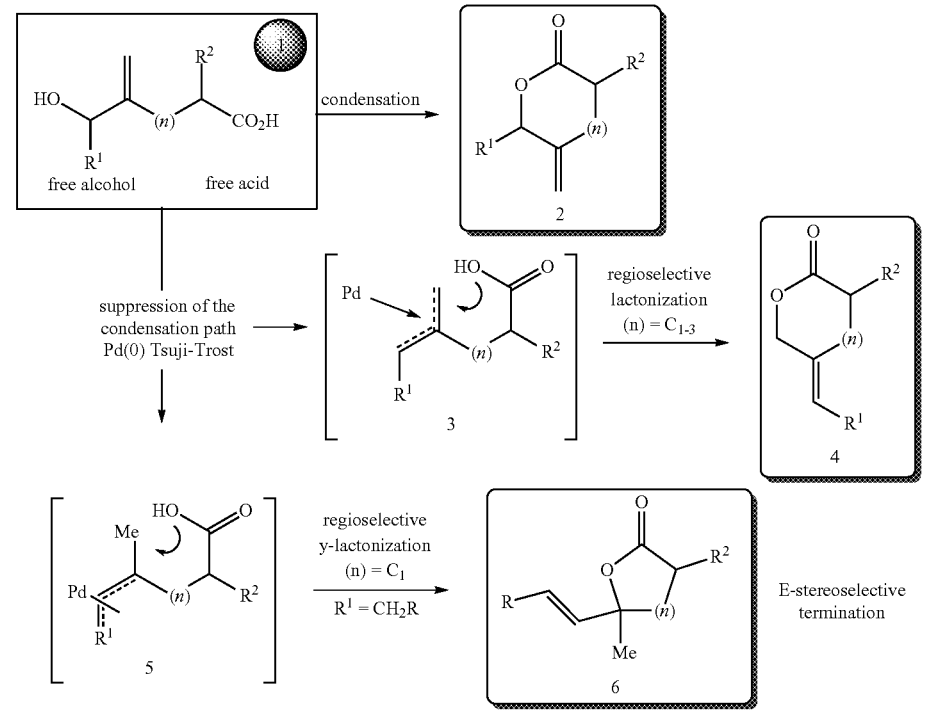

Scheme 2

- free acid as nucleophile in the presence of free alcohol
- Pd-promoted synthesis of Oxocanones, Oxepanones and Pyranones
- controlled regio- and stereoselective cyclizations
- collective precursor (prepared in 2-3 steps)

In the present invention Pd Tsuji-Trost allylation, taking place in the presence of free alcohol and free carboxylic acid as a nucleophile (see structure of 1) was employed The invention further provides the construction process of methylene lactone scaffolds of Type-4 (and its structural analogues).

The condensation suppression makes it possible to produce γ-lactone 6, via intermediate 5 (roving the palladium π-allyl complex), as shown in Scheme 2. Intriguingly, designing a method to differentiate between these allylation pathways elegantly allows, for a first time, regioselective, controlled delivery of two conceptually different methylene lactones 4 and 6.

Hydroxyalkenoic acid 11 (Table 1), was prepared in 72% yield (overall for two steps; see example section) from benzaldehyde (7; R1=Ph) and vinyl bromide[24, 25] (8;

n=CH2, R2=H), was selected as the model precursor. These studies followed the protocols designed for Pd-catalyzed allylation of classical nucleophiles.[11-13] In order to suppress the condensation pathway of 11 the reactions were carried out on a 0.2 mmol scale in the presence of a catalyst at temperatures ranging from 50 to 100° C., using a variety of bases, solvents, and other additives. Both the nature of the palladium and the ligands on the catalyst were found to affect the reaction rate.

Among catalysts studied: Pd(PPh3)4, Pd2(dba)3, Pd(OAc)2, PdCl2, and Pd(acac)2; Pd(PPh3)4 was found to be the most efficient. The other palladium sources examined led to reduction of starting precursor 11, incomplete conversion, or gave low yields of the desired tricyclic d-lactone 13 and poor allylation/condensation products (13/14) ratios. It was found that an efficient system for the desired transformation could be formed from the combination of 5.0 mol % Pd(PPh3)4 and NaOAc at 100° C. (entry 5, Scheme 2). Control experiments were performed and demonstrated that no allylation occurred in the absence of catalyst. It is notable that, under the conditions of Scheme 1, optimum results are obtained when a 1:2 molar ratio of the substrate and NaOAc is employed. Additional base has no effect on the yield. The use of toluene as the solvent provided the optimal yield of product, and allowed for a convenient protocol to be developed. It should be noted that, under the optimal set of conditions, 1H NMR analysis of the crude reaction mixture in benzene-d6 showed complete conversion of 11 generating desired d-lactone 13, effectively suppressing the condensation pathway (Table 1). The reaction profile, monitored by NMR spectroscopy, shows no formation of 14 (Table 1).[23]

A range of $R_1$-substituted hydroxyalkenoic acids were further prepared. The precursors so designed were then subjected to Pd-catalyzed cyclization conditions to provide a range of d-lactones in good yields (Scheme 3).

Scheme 3

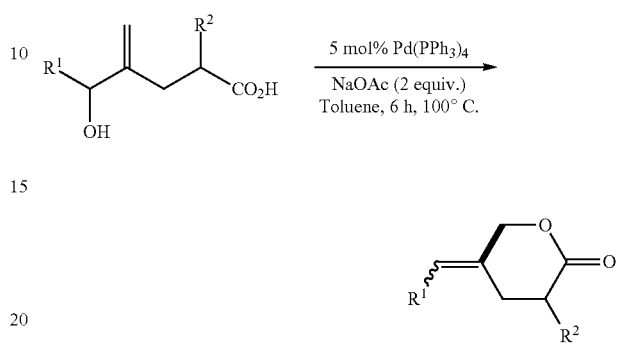

A Variation of $R^1$, $R^2$ = H

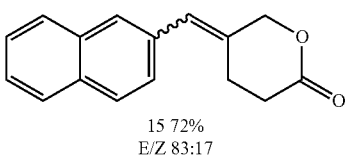

15 72%
E/Z 83:17

TABLE 1

Optimization of the Pd-promoted δ-lactonization of hydrioxyalkenoic acid: suppression of condensation

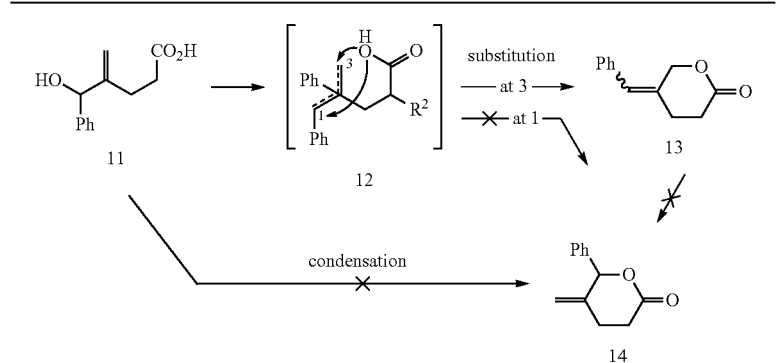

| # | Pd [5 mol %] | Base [2 eq.] | solvent | t [h] | T [° C.] | yield[b] 13/14 |
|---|---|---|---|---|---|---|
| 1 | Pd(PPh3)4 | — | toluene | 6 | 100 | 60/3 |
| 2 | Pd(PPh3)4 | K3PO4 | toluene | 6 | 100 | — |
| 3 | Pd(PPh3)4 | Cs2CO3 | toluene | 6 | 100 | — |
| 4 | Pd(PPh3)4 | K2CO3 | toluene | 6 | 100 | — |
| 5 | Pd(PPh3)4 | NaOAc | toluene | 6 | 100 | 94/0[c] |
| 6 | Pd(PPh3)4 | NaOAc | THF | 6 | 80 | 10/0 |
| 7 | Pd(PPh3)4 | NaOAc | DCE | 6 | 100 | 78/0 |
| 8 | Pd(PPh3)4 | NaOAc | dioxane | 6 | 100 | 25/10 |
| 9 | Pd(PPh3)4 | NaOAc | MeCN | 6 | 100 | 16/14 |
| 10 | Pd(PPh3)4 | NaOAc | toluene | 2 | 100 | 61/2 |
| 11 | Pd(PPh3)4 | NaOAc | toluene | 10 | 50 | 28/10 |
| 12 | Pd2(dba)3 | NaOAc | toluene | 6 | 100 | 50/3 |
| 13 | Pd(OAc)2 | NaOAc | toluene | 6 | 100 | 19/52 |
| 14 | PdCl2 | NaOAc | toluene | 12 | 100 | 34/19 |
| 15 | Pd(acac)2 | NaOAc | toluene | 6 | 100 | 25/17 |

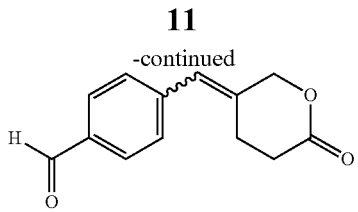

16 20% [a]
E/Z 78:22

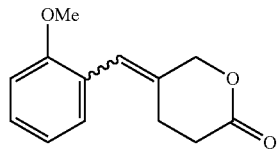

17 71%
E/Z 69:31

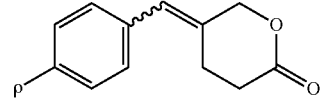

18 61%
E/Z 76:24

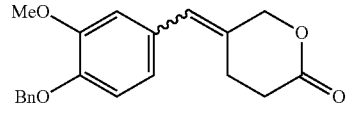

19 70%
E/Z 84:16

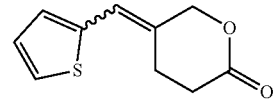

20 60%
E/Z 91:9

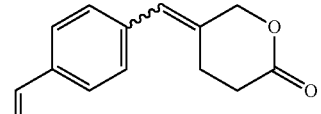

21 67%
E/Z 77:23

All the hydroxyacids, listed in Scheme 3, proved to undergo regioselective allylation, and no detectable amounts of condensation or other side products were formed. The cyclization proved to be dependent on the electronic nature of the substituted substrate. While neutral and electron-donating groups (15, 17, and 19) seem to enhance the rate, electronwithdrawing groups cause the cyclization to slow (16 and 18). The preparation of other substituted d-valerolactone scaffolds were performed (Scheme 4). In these cases, the functional modifications were performed on the alkyl chains bearing acid moieties, leaving the side benzyloxy-domain unchanged. In the presence of Pd(PPh3)4 and NaOAc, the selective cyclization of such precursors afforded the desired lactones 22-24 as single products and in good yields (Scheme 4).

Scheme 4

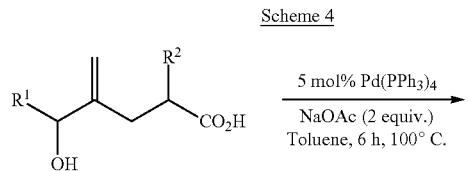

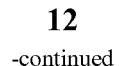

B Variation of $R^2$, $R^1$ = Ph

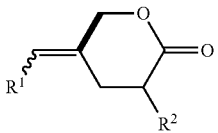

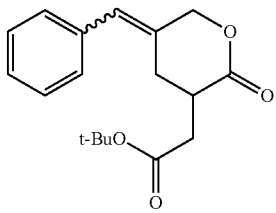

22 84%
E/Z 79:21

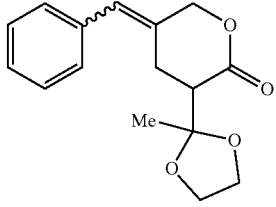

23 60%
E/Z 60:40

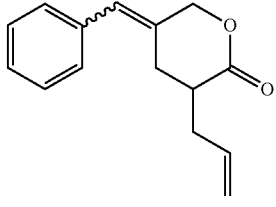

24 61%
E/Z 70:30

With suitable access to 6-terminated products, the cyclization was then extended to the synthesis of other, more challenging lactone ring sizes using (n)-modified hydroxyalkenoic acids as starting materials (Scheme 5).

Scheme 5

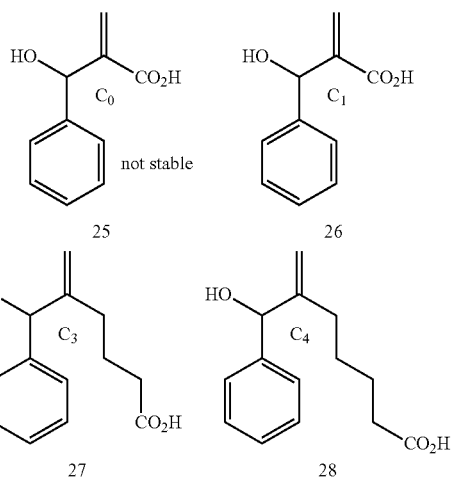

-continued

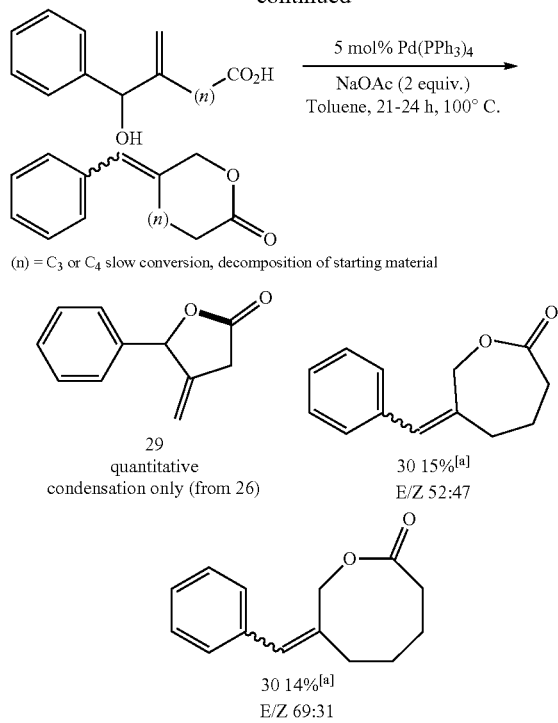

For this transformation compounds 25-28 were prepared and subjected to Pd-catalyzed conditions. Surprisingly, the optimized conditions failed to provide the expected allylation in the case of complementary precursor 25 (unstable). Alternatively, the inventors observed that hydroxyalkenoic acid 26 selectively afforded (spontaneously) the thermodynamically favored five-membered ring lactone 29, regardless of the reaction conditions applied. The reactions of 27 and 28 afforded seven- and eight-membered ring lactones as single products 30 and 31, respectively (Scheme 5), although in low yields.

In these intramolecular Pd-catalysed cyclizations incorporating 7- or 8-endo Tsuji-Trost type terminations, forming compounds such as 30 and 31, required a greater amount of time (21-24 h) and higher catalyst loading; yet, incomplete conversion, low yields, and degradation of starting material. Notwithstanding these drawbacks, the successful construction of medium ring-sized lactones via this type of Pd-catalyzed transformation is unprecedented.

In contrast to R1-substituted compounds 15-21 (Scheme 3), compound 32 did not undergo 6-lactone-type cyclization under the optimized set of conditions. Instead, the reaction proved to be highly regioselective and yielded 5-membered ring lactone 35 (Scheme 6). Such behavior was presumably attributed to the nature of the R1 substituent integrated within the hydroxyalkenoic acid scaffold: unlike the previously tested precursors, bearing aromatic R1-substituents, in this case the substituent was aliphatic.

Scheme 6

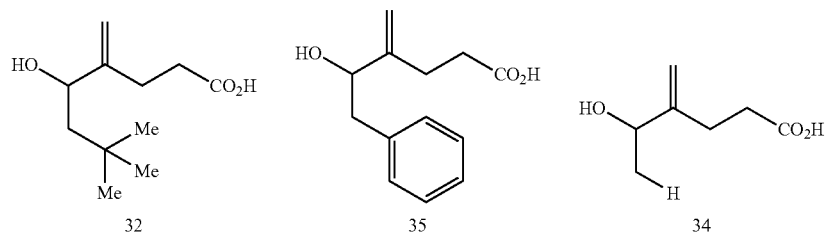

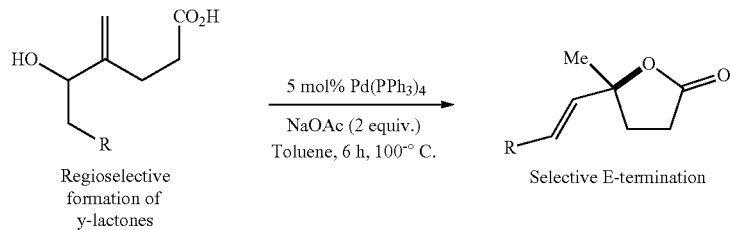

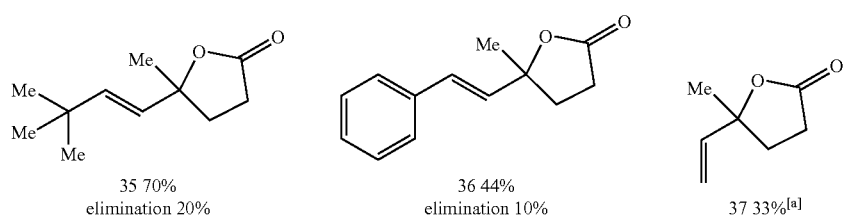

-continued

Plausable mechanistic pathways

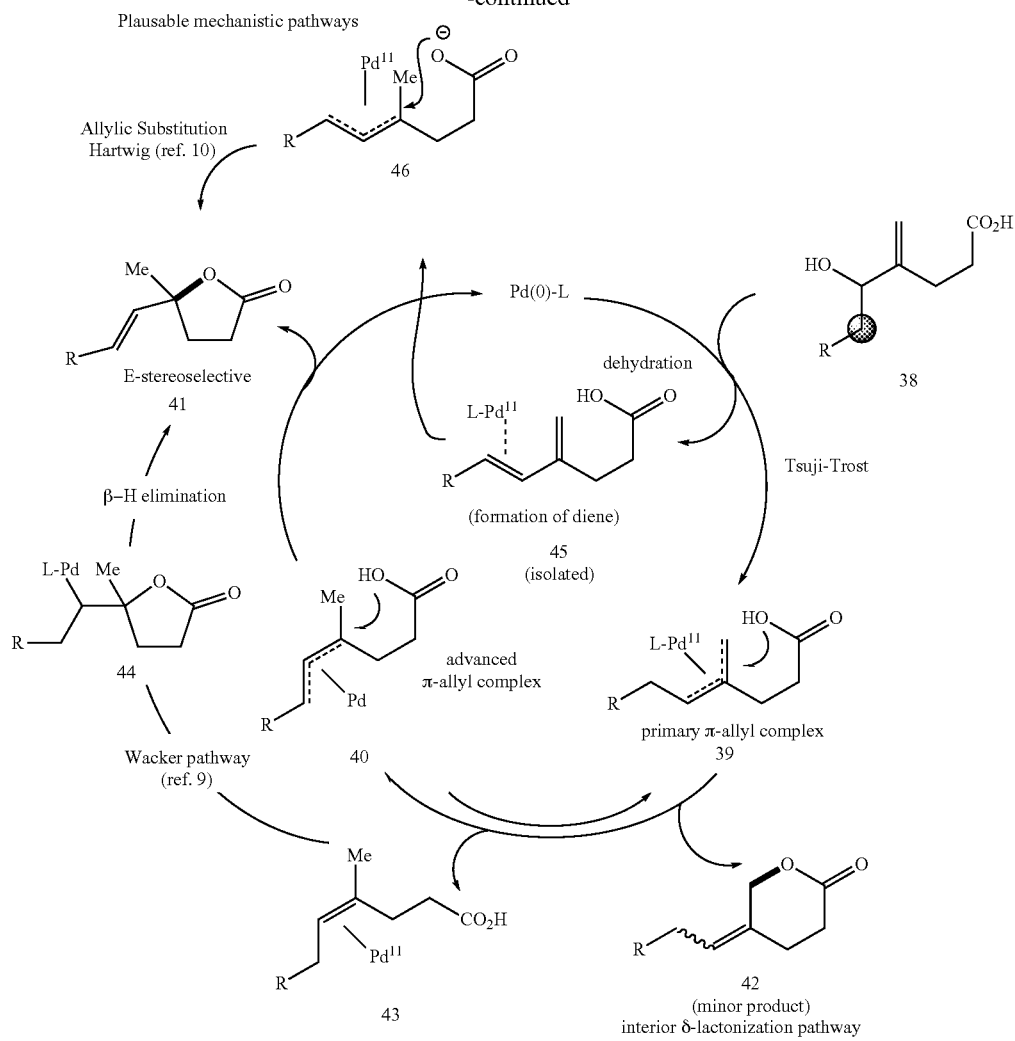

To expand the scope of substrates and targets employed, additional experiments were conducted with aliphatic R1-bearing hydroxyalkenoic acids 33 and 34 (Scheme 6) under the optimized cyclization conditions. Exclusive R1-controlled regioselectivity was detected, which led to the generation of butyrolactone scaffolds 36 and 37. It is also imperative to mention the exclusive E-selectivity observed for cyclization products 35 and 36. The entire concept offers a unique platform to efficiently and selectively produce three classes of lactone motifs (condensation, 6-endo type, or 5-exo-type termination products) that share a common starting block.

In Scheme 6 the plausible mechanisms for the transformation described above is provided. Two possible mechanisms for the palladium-assisted selective butyrolactonization of hydroxyalkenoic acid are considered. The 5-membered ring lactones syntheses are likely to be initiated by an unsaturated Pd(0)-catalyzed ionization (coordination to the double bond of 38), forming a primary π-allyl complex 39. The fact that only traces of δ-lactonization product were detected, affording mainly the g-lactone, suggests that a shift of the π-allyl complex 39 (formation of "advanced" complex 40) could have occurred, thus setting the stage for a preferred substitution. Subsequently, Pd(II)-complex 40 undergoes a b-hydride E-selective elimination to afford lactone 41. Thus, it is concluded that the presence of an aliphatic substituent allows for the π-allyl complex roving, thus suppressing the β-lactonization route (formation of 42). That being said, an alternative pathway cannot be ruled out: primary π-allyl complex 39 can undergo reduction to produce stable alkene 43, followed by oxypalladation, to yield alkyl-Pd(II)-intermediate 44. Subsequent E-oriented reductive elimination of 44 generates g-lactone product 41 and the active catalyst species. Viable participation of an intermediate 44 is supported by the observation that only E-stereoisomers were detected in the reaction mixtures.

Another notable and unexpected cyclization was achieved when hydroxyalkenoic acid 47 was subjected to the established reaction conditions (Scheme 7). To begin with, during the preparation of the acid precursor, the hydrolysis of ester 45 lead to the unforeseen isolation of stable precursor 47, instead of the anticipated acid 46. The subsequent cyclization of 47 yielded 50 as the exclusive product. Presumably, in the presence of the palladium catalyst, an equilibrium between the two p-allyl complexes 48 and 49 is established via a "chain-walking" mechanism. The following nucleophilic attack by the acid group leads to the more favorable 6-membered ring lactone 50 bearing a conjugated double bond side chain (Scheme 7).

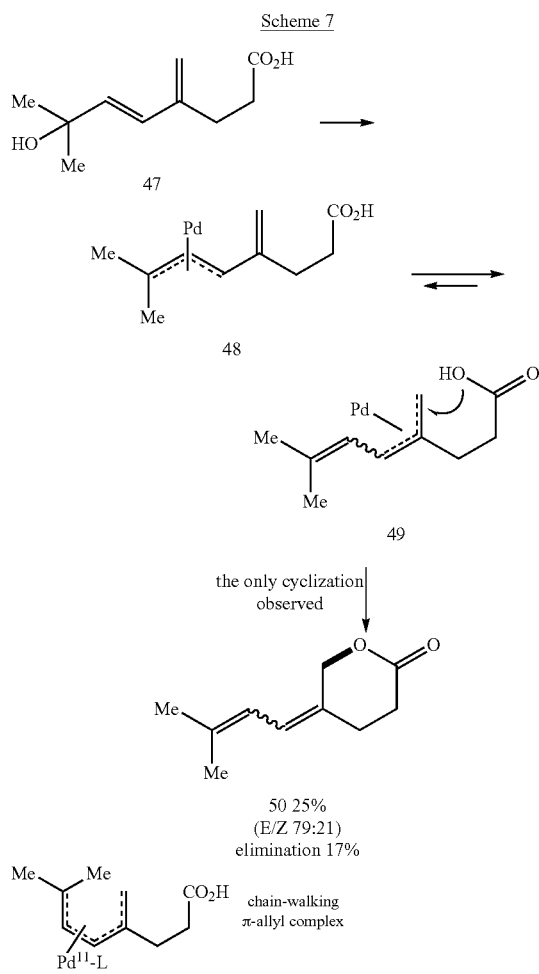

In conclusion, the inventors have developed Pd-catalyzed Tsuji-Trost like allylation reaction using unprotected alcohols and free carboxylic acids as nucleophiles, to afford methylene lactones of various ring sizes. Whereas the readily available hydroxyalkenoic acid precursors tend to undergo spontaneous condensation, under the optimized conditions of the processes of the present invention, the condensation is completely suppressed, and the transformation is steered toward the formation of differently substituted methylene lactones. Remarkably, the reaction allows the challenging construction of medium-sized lactone rings.

Experimental Section

Unless otherwise stated, all reagents were purchased from commercial suppliers and used without further purification. N-butyllithium (n-BuLi) was purchased from Sigma Aldrich as a 2.5 M solution in hexanes. Solvents used in the reactions were distilled from appropriate drying agents prior to use. Reactions were monitored by thin-layer chromatography (TLC) on silica gel 60 F254 aluminium plates (Merck) and/or gas chromatography-mass spectrometry (GCMS). Visualization of compounds on TLC was accomplished by irradiation with UV light at 254 nm and/or vanillin stain. GCMS Analysis was performed with 'Agilent 7820A' gas chromatograph equipped with 'Agilent 5975' quadrupole mass selective detector, using a Agilent HP-5MS capillary column (30 m, 0.25 mm, 0.25 µm film). Column chromatography was performed using silica gel 60 (particle size 0.040-0.063 mm) purchased from Sigma-Aldrich. Proton and carbon NMR spectra were recorded on Varian Mercury 300 MHz spectrometer in deuterated solvent. Proton chemical shifts are reported in ppm (δ) relative to tetramethylsilane with the solvent resonance employed as the internal standard (CDCl3, δ 7.26 ppm). 13C chemical shifts are reported in ppm from tetramethylsilane with the solvent resonance as the internal standard (CDCl$_3$, δ 77.0 ppm). Data are reported as follows: chemical shift, multiplicity (s=singlet, d=doublet, t=triplet, q=quartet, m=multiplet), integration and coupling constants (Hz). High resolution mass spectra were determined on a Thermo Scientific LTQ Orbitrap XL (FTMS). Infrared (IR) spectra were recorded on a ThermoFischer Scientific NICOLET iS10 spectrometer.

Unless otherwise noted, the diastereomeric ratios were calculated from NMR analysis of the crude reaction mixture. Abbreviations: THF (tetrahydrofuran), n-BuLi (n-Butyllithium), DMF (dimethylformamide), dr (diastereomeric ratio), LDA (lithium diisopropylamide), DMSO (dimethyl sulfoxide).

Synthesis of Precursors:

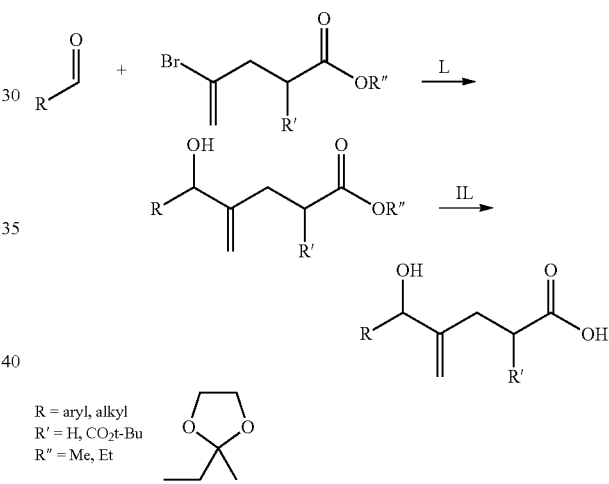

General Procedure B

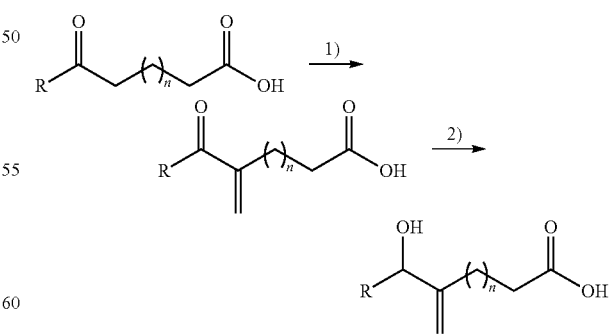

General Procedure A:i. To the solution of aldehyde (1.0 equiv) in dry DMF (0.125 M) was added CrCl2 (3.2 equiv), NiCl2 (0.2 equiv), and vinyl bromide (1.5 equiv) under nitrogen atmosphere. The reaction was stirred for 4 h at room temperature. The reaction was quenched with 1 M serine solution in saturated NaHCO$_3$(4 mL/mmol) at 0° C. and stirred until the solution turned purple. Excess water was added and the mixture was extracted with diethyl ether. The organic layer was dried and concentrated under vacuum. The crude product was subjected to hydrolysis without further purification. ii. Hydrolysis: An aqueous solution of KOH (4 equiv, 0.5 M) and MeOH (0.1 M) were added and stirred at 60° C. for 3 h. Methanol was removed under vacuum, and the resulting solution was acidified (pH ~2) with 1 M HCl and extracted with ethyl acetate. The volatiles were removed and the crude product was purified by silica gel flash column chromatography.

General Procedure B: 1) To a solution of corresponding acid (1.0 equiv) in pyridine (1.2 M) was added paraformaldehyde (3.0-6.0 equiv) and piperidine (0.2-0.4 equiv). (I. Sivák, D. Berkeš, J. Kožíšek, A. Kolarovič, *Tetrahedron Lett.* 2016, 57, 1079-1082) The reaction was stirred for 12-48 h at 70° C. and monitored by TLC. The reaction was quenched with a 3 M H2SO4 solution. Excess water was added and the mixture was extracted with diethyl ether. The combined organic layers were dried and concentrated under vacuum. As confirmed by NMR, the crude product was found to be sufficiently clean, and was subjected to reduction without further purification. 2) Reduction: To the solution of acid (1.0 equiv) in methanol (0.3 M) NaBH4 was added portionwise (4.0-6.0 equiv. in total) at 0° C. The reaction was stirred for 1 h at 0° C. and then for 0.5 h at room temperature. Methanol was removed under vacuum and the resulting solution was acidified (pH~2) with 1 M HCl and extracted with diethyl ether. The volatiles were removed and the crude product was purified by silica gel flash column chromatography.

Synthesis of Vinyl Bromides:

4-bromopent-4-enoate

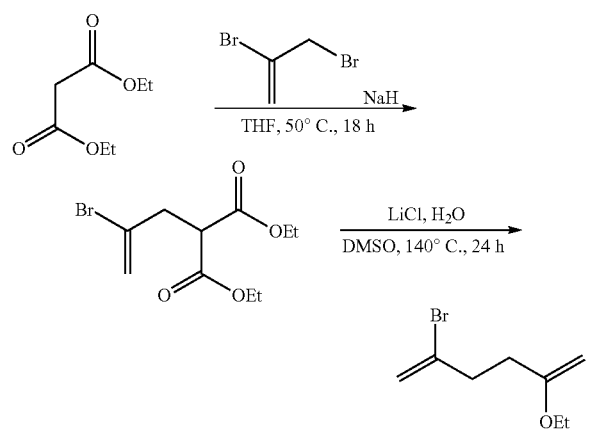

Diethyl malonate (1.5 equiv) was added dropwise to a solution of NaH (1.35 equiv) in dry THF (0.15 M) at room temperature. The mixture was stirred for 1 h at ambient temperature, until all solids were dissolved. The reaction mixture was cooled to 0° C., and 2,3-dibromopropene (1.0 equiv) was added dropwise. The temperature was raised to 50° C. and the reaction was allowed to stir for 18 h. The reaction was quenched with NH4Cl and excess water was added. The mixture was extracted with ethyl acetate, and the combined organic layers were dried and concentrated under vacuum. The crude product was dissolved in DMSO (0.5 M), followed by addition of LiCl (2.0 equiv) and H2O (1 equiv). The mixture was stirred at 140° C. and the progress of the reaction was monitored by TLC/GC. After 24 h, excess water was added and the mixture was extracted with ethyl acetate. The combined organic layers were dried and concentrated under vacuum. The crude product was purified by silica gel column chromatography (8% ethyl acetate in hexane) or by vacuum distillation. The typical yield is 32% over two steps.

4-(tert-butyl) 1-ethyl 2-(2-bromoallyl)succinate

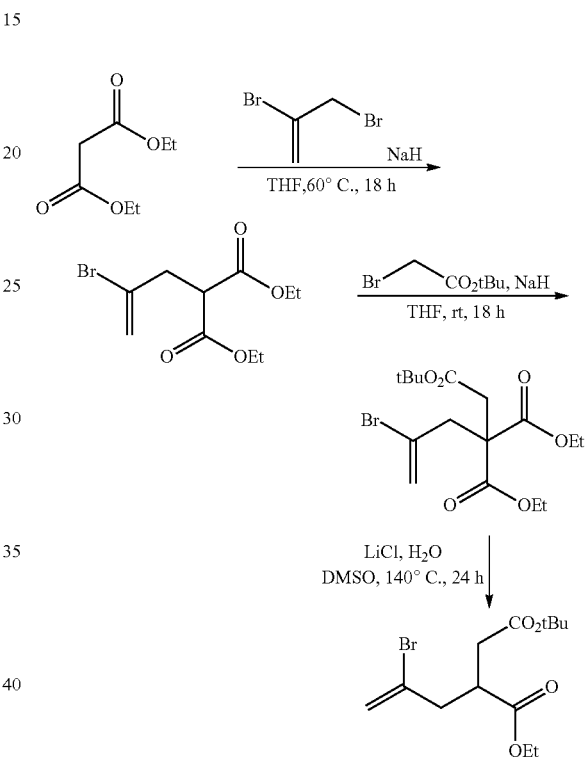

Diethyl malonate (1.5 equiv, 24.0 mmol 3.64 mL) was added dropwise to a solution of NaH (1.35 equiv, 21.5 mmol, 0.86 g, 60% in oil) in dry THF (140 mL) at room temperature. The mixture was stirred for 1 h at ambient temperature, until all solids were dissolved. The reaction mixture was cooled to 0° C., and 2,3-dibromopropene (1.0 equiv, 16.0 mmol, 1.6 mL) was added dropwise. The temperature was raised to 50° C. and the reaction was allowed to stir for 18 h. The reaction was quenched with NH4Cl and excess water was added. The mixture was extracted with ethyl acetate, and the combined organic layers were dried and concentrated under vacuum. The crude product was purified by silica gel column chromatography (5% ethyl acetate in hexane) to give pure diethyl 2-(2-bromoallyl) malonate (9.6 mmol, 2.7 g, 60%, yellow oil). A solution of diethyl 2-(2-bromoallyl)malonate (0.72 mmol, 1.0 equiv, 0.200 mg) in THF (1 M, 0.7 mL) was cooled to 0° C., followed by portionwise addition of NaH (0.72 mmol, 1.0 equiv, 0.029 g). The mixture was stirred for 30 min at ambient temperature, until all solids were dissolved. The reaction mixture was cooled to 0° C., and tert-butyl bromoacetate (0.79 mmol, 1.0 equiv, 117 µL) was added dropwise. The temperature was raised to room temperature and the reaction was allowed to stir for 18 h. The reaction was quenched with NH4Cl and water was added. The mixture was extracted with ethyl acetate, and the combined organic layers were dried and concentrated under vacuum. The crude product (0.56 mL, 1.0 equiv, 0.219 g) was dissolved in DMSO (1.1 mL), followed by addition of LiCl (1.12 mmol, 2.0 equiv, 0.047 g) and H2O (0.56 mmol, 1.0 equiv, 10 μL). The mixture was stirred at 140° C. and the progress of the reaction was monitored by TLC/GC. After 24 h, excess water was added and the mixture was extracted with diethyl ether. The combined organic layers were dried and concentrated under vacuum. The crude product was purified by silica gel column chromatography (10% ethyl acetate in hexane) to give 4-(tert-butyl) 1-ethyl 2-(2-bromoallyl)succinate (0.30 mmol, 43% over two steps, 0.108 mg, clear oil).

Ethyl 4-bromo-2-(2-methyl-1,3-dioxolan-2-yl)pent-4-enoate

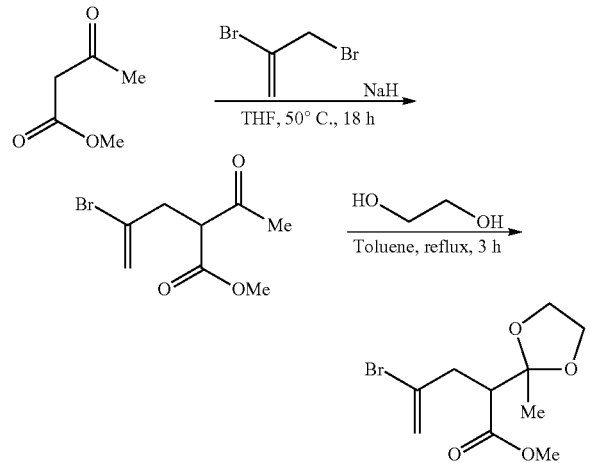

Methyl 3-oxobutanoate (1.5 equiv, 30.0 mmol, 3.48 g) was added dropwise to a solution of NaH (1.35 equiv, 27.0 mmol, 1.08 g, 60% in oil) in dry THF (160.0 mL) at room temperature. The mixture was stirred for 1 h at ambient temperature, until all solids were dissolved. The reaction mixture was cooled for 0° C., and 2,3-dibromopropene (1.0 equiv, 2.0 mmol, 1.94 mL) was added dropwise. The temperature was raised to 50° C. and the reaction was allowed to stir for 18 h. The reaction was quenched with NH4Cl and excess water was added. The mixture was extracted with ethyl acetate and the combined organic layers were dried and concentrated under vacuum. Part of the crude product (2.0 g, ca. 8.5 mmol) was dissolved in toluene (40 mL), followed by addition of ethylene glycol (5.0 equiv, 42.5 mmol, 2.63 g) and p-toluenesulfonic acid (0.1 equiv, 0.85 mmol, 0.15 g). The flask was equipped with Dean-Stark apparatus, and the reaction mixture was refluxed for 3 h. Next, the solution was concentrated under vacuum and purified by silica gel column chromatography (20% ethyl acetate in hexane) to give pure methyl 4-bromo-2-(2-methyl-1,3-dioxolan-2-yl)pent-4-enoate (1.1 g, 4.0 mmol, 47% over two steps).

Synthesis of Substrates:

11: 4-(hydroxy(phenyl)methyl)pent-4-enoic acid

General procedure A was applied using ethyl 4-bromopent-4-enoate (25.00 mmol, 5.18 g), CrCl2 (53.31 mmol, 6.55 g), NiCl2 (3.33 mmol, 0.43 g), and benzaldehyde (16.66 mmol, 2.02 mL). The intermediate product was hydrolyzed by using 0.5 M aqueous solution of KOH (66.64 mmol). Purification of the crude product by silica gel flash column chromatography (10% isopropanol in hexane) yielded pure 4-(hydroxy(phenyl)methyl)pent-4-enoic acid (2.46 g, 72% yield, white solid). M.p. 75-77° C. 1H NMR (300 MHz, CDCl3): δ 7.28-7.39 (m, 5H), 5.21 (s, 1H), 5.31 (s, 1H), 4.99 (s, 1H), 2.52-2.16 (m, 4H). 13C NMR (75 MHz, CDCl$_3$): δ 178.8, 149.0, 141.6, 128.5, 127.8, 126.4, 111.2, 77.4, 32.3, 25.9. IR (neat): 2926, 1708, 1645, 1610, 1493, 1450, 1153, 1024, 925, 835 cm-1. HRMS (n/z) calcd for C12H14O3Na ([M+Na]+): 229.0835; found: 229.0836.

Hydroxy acid a: 4-(hydroxy(naphthalen-2-yl)methyl)pent-4-enoic acid

General procedure A was applied using ethyl 4-bromopent-4-enoate (6.00 mmol, 1.24 g), CrCl2 (12.80 mmol, 1.57 g), NiCl2 (0.80 mmol, 0.10 g), and naphthaldehyde (4.00 mmol, 0.462 g). The intermediate product was hydrolyzed by using 0.5 M aqueous solution of KOH (16.00 mmol). Purification of the crude product by silica gel flash column chromatography (20% isopropanol in hexane) yielded pure 4-(hydroxy(naphthalen-2-yl)methyl)pent-4-enoic acid (0.25 g, 25% yield, yellow solid). M.p. 112-116° C. 1H NMR (300 MHz, CDCl3): δ 7.91-7.72 (m, 4H), 7.54-7.36 (m, 3H), 5.40-5.26 (m, 2H), 5.02 (s, 1H), 2.55-2.42 (m, 2H), 2.39-2.10 (m, 2H). 13C NMR (75 MHz, CDCl3): δ 179.0, 148.9, 138.9, 133.2, 132.9, 128.3, 128.0, 127.7, 126.2, 125.9, 125.3, 124.4, 111.6, 77.5, 32.39, 25.9. IR (neat): 3290, 2901, 2643, 1684, 1293, 900 cm-1. HRMS (m/z) calcd for C16H16O3Na ([M+Na]+): 279.0997; found: 279.0985.

Hydroxy acid b: 4-((4-formylphenyl)(hydroxy)methyl)pent-4-enoic acid

General procedure A was applied using ethyl 4-bromopent-4-enoate (4.50 mmol, 0.93 g), CrCl2 (9.60 mmol, 1.18 g), NiCl2 (0.9 mmol, 0.077 g), and 4-(1,3-dioxolan-2-yl)benzaldehyde (3.00 mmol, 0.53 g). The intermediate product was hydrolyzed by using 0.5 M aqueous solution of KOH (12.00 mmol). Purification of the crude product by silica gel flash column chromatography (20% isopropanol in hexane) yielded pure 4-((4-formylphenyl)(hydroxy)methyl)pent-4-enoic acid (0.28 g, 40% yield, white solid). 1H NMR (300 MHz, CDCl3): δ10.00-9.92 (s, 1H), 7.89-7.72 (m, 2H), 7.59-7.47 (m, 2H) 5.32-5.22 (m, 2H), 5.02-4.95 (s, 1H), 2.55-2.39 (m, 2H), 2.29-2.21 (m, 1H), 2.21-1.99 (m, 1H). 13C NMR (75 MHz, CDCl3): δ 192.3, 178.3, 148.6, 148.5, 135.5, 129.9, 126.9, 112.6, 77.2, 32.2, 25.3 IR (neat): 3350, 2989, 1705, 1651, 1601, 1570, 1201, 1047, 832 cm-1. HRMS (m/z) calcd for C13H14O4 ([M+H]+): 234.0892; found: 234.0866.

Hydroxy acid c: 4-(hydroxy(3-methoxyphenyl)methyl)pent-4-enoic acid

General procedure A was applied using ethyl 4-bromopent-4-enoate (3.00 mmol, 0.64 g), CrCl2 (6.40 mmol, 0.79 g), NiCl2 (0.6 mmol, 0.05 g), and omethoxybenzaldehyde (4.00 mmol, 0.53 g). The intermediate product was hydrolyzed by using 0.5 M aqueous solution of KOH (12.00 mmol). Purification of the crude product by silica gel flash column chromatography (10% isopropanol in hexane) yielded pure 4-(hydroxy(3-methoxyphenyl)methyl)pent-4-enoic acid (0.34 g, 64% yield, clear oil). The compound slowly spontaneously condensed at room temperature. 1H NMR (300 MHz, CDCl3): δ 7.35-7.18 (m, 2H), 7.06-6.81 (m, 2H), 5.47-5.37 (s, 1H), 5.24-5.11 (m, 1H), 5.00-4.89 (s, 1H), 3.86-3.79 (s, 3H), 2.59-2.41 (m, 2H), 2.41-2.20 (m, 2H). 13C NMR (75 MHz, CDCl3): δ 178.8, 156.9, 148.5, 129.7, 128.9, 127.7, 120.1, 110.7, 72.2, 55.4, 32.5, 27.3. IR (neat): 3490, 2938, 1707, 1600, 1489, 1241, 1027 cm-1. HRMS (m/z) calcd for C13H16O4Na ([M+Na]+): 259.0941; found: 259.0938.

Hydroxy acid d: 4-((4-fluorophenyl)(hydroxy)methyl)pent-4-enoic acid

General procedure A was applied using ethyl 4-bromopent-4-enoate (6.00 mmol, 1.24 g), CrCl2 (12.80 mmol, 1.57 g), NiCl2 (0.80 mmol, 0.10 g), and pfluorobenzaldehyde (4.00 mmol, 0.43 mL). The intermediate product was hydrolyzed by using 0.5 M aqueous solution of KOH (16.00 mmol). Purification of the crude product by silica gel flash column chromatography (10% isopropanol in hexane) yielded pure 4-((4-fluorophenyl)(hydroxy)methyl)pent-4-enoic acid (0.60 g, 67% yield, gummy liquid). 1H NMR (300 MHz, CDCl3): δ 7.31-6.96 (m, 4H), 5.24 (s, 1H), 5.13 (s, 1H), 4.95 (s, 1H), 2.47-2.10 (m, 4H). 13C NMR (75 MHz, CDCl3): δ 178.8, 162.2 (d, 1J(F-C)=244.5 Hz), 148.8, 137.2 (d, 4J(F-C)=3.8 Hz), 128.1 (d, 3J(F-C)=8.3 Hz), 115.2 (d, 2J(F-C)=21.8 Hz), 76.6, 32.3 and 25.7. 19FNMR (282 MHz, CDCl3): δ-62.7. IR (neat): 3160, 2926, 1708, 1646, 1603, 1507, 1413, 1267, 1220, 1182, 1156, 1050, 1040, 909, 833 cm-1. HRMS (m/z) calcd for C12H13FO3Na ([M+Na]+): 247.0740; found: 247.0742.

Hydroxy acid e: 4-((4-(benzoyloxy)-3methoxyphenyl)(hydroxy)methyl)pent-4-enoic acid General procedure A was applied using ethyl 4-bromopent-4-enoate (4.50 mmol, 0.93 g), CrCl2 (9.60 mmol, 1.18 g), NiCl2 (0.9 mmol, 0.077 g), and 4-(benzyloxy)-3-methoxybenzaldehyde (3.00 mmol, 0.73 g). The intermediate product was hydrolyzed by using 0.5 M aqueous solution of KOH (12.00 mmol). Purification of the crude product by silica gel flash column chromatography (20% isopropanol in hexane) yielded pure 4-((4-(benzoyloxy)-3-methoxyphenyl)(hydroxy)methyl)pent-4-enoic acid (0.31 g, 33% yield, yellow liquid). 1H NMR (300 MHz, CDCl3): δ 7.47-7.27 (m, 5H), 6.97-6.87 (m, 1H), 6.87-6.75 (m, 2H), 6.25-5.90 (broad s, 1H), 5.29 (s, 1H), 5.17-5.07 (m, 3H), 4.97 (s, 1H), 3.87 (s, 3H), 2.53-2.40 (m, 2H), 2.38-2.08 (m, 2H). 13C NMR (75 MHz, CDCl3): δ 178.7, 149.6, 149.2, 147.7, 137.1, 134.8, 128.5, 127.8, 127.2, 118.9, 113.6, 110.8, 110.0, 77.1, 71.0, 55.9, 32.5, 26.2 IR (neat): 3450, 2936, 1708, 1508, 1258, 1135, 1022 cm-1. HRMS (m/z) calcd for C20H22O5: 343.1467; found: 343.1539.

Hydroxy acid f: 4-(hydroxy(thiophen-2-yl)methyl)pent-4-enoic acid

General procedure B was applied using 5-oxo-5-(thiophen-2-yl)pentanoic acid (1.0 equiv, 10.1 mmol, 2.0 g), paraformaldehyde (3.0 equiv, 30.3 mmol, 0.910 g), piperidine (0.2 equiv, 2.2 mmol, 0.22 ml), and pyridine (9 ml). The solution was stirred for 24 h, followed by workup. The intermediate product (3.7 mmol, 0.80 g) was reduced with NaBH4 (4 equiv, 15.0 mmol, 0.55 g). Purification of the crude product by silica gel flash column chromatography (5% isopropanol in hexane) yielded pure 4-(hydroxy(thiophen-2-yl)methyl)pent-4-enoic acid (0.366 g, 38% yield over two steps, white wax). Starting material was recovered. 1H NMR (300 MHz, CDCl3): δ 7.32-7.21 (m, 1H), 7.03-6.88 (m, 2H), 5.45 (s, 1H), 5.36 (s, 1H), 5.02 (s, 1H), 2.58-2.47 (m, 2H), 2.47-2.19 (m, 2H) 13C NMR (75 MHz, CDCl3): δ 178.5, 148.7, 148.2, 126.8, 125.3, 124.9, 111.4, 73.5, 32.4, 25.9 IR (neat): 3450, 2923, 1705, 1411, 1214 cm-1. HRMS (n/z) calcd for C10H12O3S ([M+H]+): 212.0507; found: 212.0500.

Hydroxy acid g: 4-(hydroxy(4-vinylphenyl)methyl)pent-4-enoic acid

General procedure A was applied using ethyl 4-bromopent-4-enoate (6.00 mmol, 1.24 g), CrCl2 (12.80 mmol, 1.57 g), NiCl2 (0.80 mmol, 0.10 g), and p-vinylbenzaldehyde (4.00 mmol, 0.53 g). The crude was purified by flash column chromatography (10% EtOAc in hexane) to give ester product (0.75 g, 72%, 0.29 mmol). Ester was hydrolyzed by using 0.5 M aqueous solution of KOH (11.60 mmol). Purification of the crude product by silica gel flash column chromatography (10% isopropanol in hexane) yielded pure 4-(hydroxy(4-vinylphenyl)methyl)pent-4-enoic acid (0.20 g, 27% yield, white solid). A polymerization resin was also isolated. 1H NMR (300 MHz, CDCl3): δ 7.43-7.25 (m, 4H), 6.78-6.62 (m, 1H), 5.82-5.67 (m, 1H), 5.32-5.21 (m, 2H), 5.17 (s, 1H), 4.97 (s, 1H), 2.53-2.41 (m, 2H), 2.41-2.05 (m, 2H). 13C NMR (75 MHz, CDCl3): δ 179.0, 148.9, 141.1, 137.0, 136.4, 126.7, 126.3, 113.9, 111.2, 77.1, 32.4, 25.9. IR (neat): 3395, 2916, 1728, 1650, 901 cm-1. HRMS (m/z) calcd for C14H16O3Na ([M+Na]+): 255.0992; found: 255.0991.

Hydroxy acid h: 2-(2-(tert-butoxy)-2-oxoethyl)-4-(hydroxy(phenyl)methyl)pent-4-enoic acid General procedure A was applied using 4-(tert-butyl) I-ethyl 2-(2-bromoallyl)succinate (3.70 mmol, 1.2 g), CrCl2 (7.9 mmol, 0.97 g), NiCl2 (0.49 mmol, 0.062 g), and benzaldehyde (2.5 mmol, 0.26 g). The intermediate was isolated by silica gel flash column chromatography (20% EtOAc in hexane) to give the corresponding ester (0.59 g, 69%), which was then hydrolyzed by using 0.5 M aqueous solution of KOH (6.9 mmol). Purification of the crude product by silica gel flash column chromatography (10% isopropanol in hexane) yielded pure 2-(2-(tert-butoxy)-2-oxoethyl)-4-(hydroxy(phenyl)methyl)pent-4-enoic acid as a mixture of diastereoisomers (0.280 g, 51% yield, dr 55:45, white solid). M.p. 108-111° C. 1H NMR (300 MHz, CDCl$_3$, mixture of diastereomers): δ 7.40-7.21 (m, 5H), 5.88 (d, J=17.3 Hz, 1H), 5.28-5.04 (m, 1H), 5.04-4.57 (m, 1H), 3.32-2.78 (m, 2H), 2.77-2.05 (m, 3H), 1.53-1.30 (m, 9H) 13C NMR (75 MHz, CDCl3, overall for two diastereoisomers): δ 173.2, 172.8, 170.7, 170.3, 142.0, 139.7, 137.8, 136.8, 128.7, 128.5, 128.4, 127.3, 126.3, 126.2, 115.6, 114.6, 83.8, 82.7, 81.2, 36.9, 36.8, 36.7, 36.2, 32.0, 31.7, 28.0. IR (neat): 3500, 2977, 1725, 1366, 1140 cm-1. HRMS (m/z) calcd for C18H24O5Na ([M+Na]+): 343.1516; found: 343.1516.

Hydroxy acid i: 4-(hydroxy(phenyl)methyl)-2-(2-methyl-1,3-dioxolan-2-yl)pent-4-enoic acid General procedure A was applied using ethyl 4-bromo-2-(2-methyl-1,3-dioxolan-2-yl)pent-4-enoate (3.90 mmol, 0.93 g), CrCl2 (8.3 mmol, 1.02 g), NiCl2 (0.52 mmol, 0.066 g), and benzaldehyde (2.6 mmol, 0.53 g). The intermediate product was isolated by silica gel flash column chromatography (20% EtOAc in hexane) to give the corresponding ester (0.30 g, 41%), which was then hydrolyzed by using 0.5 M aqueous solution of KOH (4.00 mmol). Purification of the crude product by silica gel flash column chromatography (10% isopropanol in hexane) yielded pure 4-(hydroxy(phenyl)methyl)-2-(2-methyl-1,3-dioxolan-2-yl)pent-4-enoic acid as a mixture of two diastereoisomers (0.19 g, 65% yield, dr 85:15, clear oil). 1H NMR (300 MHz, CDCl₃, mixture of diastereomers): δ 7.39-7.29 (m, 5H), 5.28 (s, 1H), 5.21 (s, 1H), 5.05 (s, 1H), 4.02-3.82 (m, 4H), 3.02-2.84 (m, 1H), 2.57-2.39 (m, 1H), 2.26-2.07 (m, 1H), 1.35 (s, 3H) 13C NMR (75 MHz, CDCl3, major diastereoisomer): δ 176.5, 147.9, 141.5, 128.4, 127.6, 126.4, 113.1, 109.3, 76.9, 64.8, 52.8, 29.3, 21.6 IR (neat): 3467, 2950, 1731, 1435, 1201, 1037 cm-1. HRMS (m/z) calcd for C16H20O5Na ([M+Na]+): 315.1208; found: 315.1192.

Hydroxy acid j:
2-allyl-4-(hydroxy(phenyl)methyl)pent-4-enoic acid

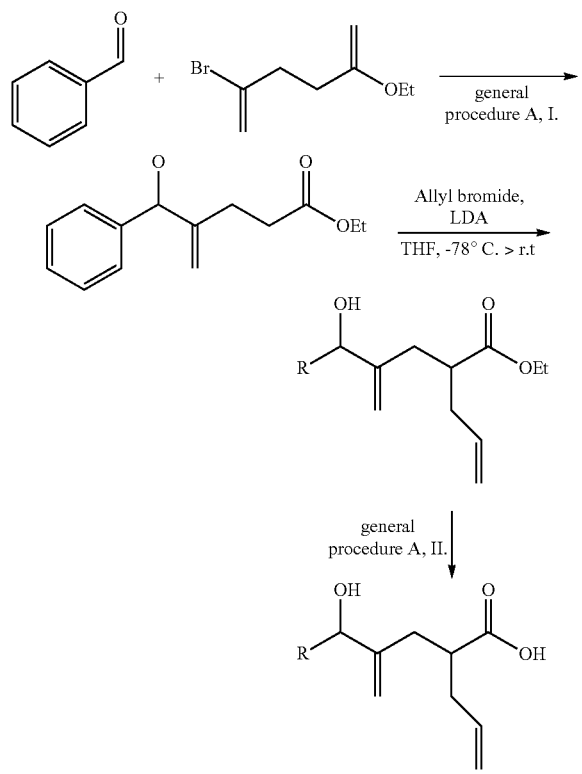

General procedure A was applied using ethyl 4-bromopent-4-enoate (6.00 mmol, 1.24 g), CrCl2 (12.80 mmol, 1.57 g), NiCl2 (0.80 mmol, 0.10 g), and pbenzaldehyde (4.00 mmol, 0.43 mL). The intermediate ester was added dropwise to a solution of in situ prepared LDA (2.0 equiv, 8.0 mmol) at −78-C. The mixture was stirred for 1 h, and then allyl bromide (2.5 equiv, 9.25 mmol, 0.84 mL) was added dropwise −78-C. The mixture was slowly warmed to room temperature and stirred for 12 h. The reaction was quenched with NH4Cl, extracted with EtOAc, dried with Na2SO4, and concentrated under reduced pressure. Purification of the residue by silica gel flash column chromatography (30% EtOAc in hexane) yielded ethyl 2-allyl-4-(hydroxy(phenyl)methyl)pent-4-enoate (0.170 g, 0.62 mmol, 16% over 2 steps). The ester product was hydrolyzed by using 0.5 M aqueous solution of KOH (2.5 mmol). Purification of the crude product by silica gel flash column chromatography (10% isopropanol in hexane) yielded 2-allyl-4-(hydroxy(phenyl)methyl)pent-4-enoic acid as a mixture of two diastereomers (120 mg, 74%, dr 60:40, yellow oil). 1H NMR (300 MHz, CDCl3, mixture of diastereomers): δ 7.51-7.23 (m, 5H), 5.81-5.53 (m, 1H), 5.34-5.22 (m, 1H), 5.22-5.13 (m, 1H), 5.13-4.95 (m, 3H), 2.84-2.60 (m, 1H), 2.42-1.96 (m, 4H). 13C NMR (75 MHz, CDCl₃): major diastereoisomer: δ 180.1, 147.9, 141.5, 128.4, 127.7, 126.5, 117.4, 112.7, 77.6, 44.04, 36.2, 33.1; minor diastereoisomer, characteristic peaks: 134.6, 113.2, 77.4, 44.2, 34.1. IR (neat): 3470, 1706, 1448, 1188, 912 cm-1. HRMS (m/z) calcd for C15H18O3: 246.1256; found: 246.1242.

25: 2-(hydroxy(phenyl)methyl)acrylic acid

Compound was prepared according to literature procedure (N. R. Siegfried E. Drewes, Neville D. Emslie, John S. Field, Abdullah A. Khan, *Assymetry* 1992, 3, 255-260).

27: 5-(hydroxy(phenyl)methyl)hex-5-enoic acid

General procedure B was applied using 6-oxo-6-phenylhexanoic acid (1.0 equiv, 4.9 mmol, 1.0 g), paraformaldehyde (3.0 equiv, 14.6 mmol, 0.47 g), piperidine (0.2 equiv, 1.0 mmol, 0.1 ml), and pyridine (4.5 mL). The solution was stirred for 24 h, followed by workup. The intermediate product (4.9 mmol) was reduced with NaBH4 (6 equiv, 29.4 mmol, 1.18 g). Purification of the crude product by silica gel flash column chromatography (5% isopropanol in hexane) yielded pure 5-(hydroxy(phenyl)methyl)hex-5-enoic acid (0.760 g, 70% yield over two steps, pale yellow oil). 1H NMR (300 MHz, CDCl3): δ 7.42-7.27 (m, 5H), 5.29 (s, 1H), 5.16 (s, 1H), 4.99 (s, 1H), 2.41-2.15 (m, 2H), 2.12-1.83 (m, 2H), 1.83-1.65 (m, 2H). 13C NMR (75 MHz, CDCl3): δ 179.3, 149.6, 141.8, 128.4, 127.8, 126.6, 110.8, 77.2, 33.3, 30.9, 22.6. IR (neat): 3350, 2937, 1703, 1493, 699 cm-1. HRMS: (m/z) calcd for C13H16O3Na ([M+Na]+): 243.0992; found: 243.0991.

28: 6-(hydroxy(phenyl)methyl)hept-6-enoic acid

General procedure B was applied using 6-oxo-6-phenylhexanoic acid (1.0 equiv, 4.5 mmol, 1.0 g), paraformaldehyde (6 equiv, 27.0 mmol, 0.81 g), piperidine (1.8 mmol, 0.175 mL), and pyridine (4.5 mL). Solution was stirred for 48 h, followed by workup. The crude product was reduced with NaBH4 (6 equiv, 27.0 mmol, 1.18 g). Purification by silica gel flash column chromatography (15% isopropanol in hexane) yielded pure 6-(hydroxy(phenyl)methyl)hept-6-enoic acid (0.760 g, 66% yield over two steps, clear oil). 1H NMR (300 MHz, CDCl3): δ 7.38-7.23 (m, 5H), 5.27 (s, 1H), 5.14 (s, 1H), 4.97 (s, 1H), 2.36-2.20 (m, 2H), 2.09-1.77 (m, 2H), 1.68-1.50 (m, 2H), 1.50-1.37 (m, 2H). 13C NMR (75 MHz, CDCl3): δ 179.6, 150.3, 141.9, 128.4, 127.7, 126.6, 110.2, 77.3, 33.7, 31.2, 27.0, 24.5. IR (neat): 3470, 2934, 1704, 1230, 907 cm-1. HRMS: (m/z) calcd for C14H18O3Na ([M+Na]+): 257.1154; found: 257.1149.

32: 5-hydroxy-7,7-dimethyl-4-methyleneoctanoic acid

General procedure A was applied using ethyl 4-bromopent-4-enoate (4.50 mmol, 0.93 g), CrCl2 (9.60 mmol, 1.18 g), NiCl2 (0.9 mmol, 0.077 g), and 3,3-dimethylbutanal (3.00 mmol, 0.3 g). The intermediate product was hydrolyzed by using 0.5 M aqueous solution of KOH (12.00 mmol). Purification of the crude product by silica gel flash column chromatography (15% isopropanol in hexane) yielded pure 5-hydroxy-7,7-dimethyl-4-methyleneoctanoic acid (0.14 g, 23% yield over two steps, white wax). The compound undergoes fast self-condensation at room temperature. 1H NMR (300 MHz, CDCl3): δ 5.08 (s, 1H), 4.80 (s, 1H), 4.31-4.15 (m, 1H), 2.63-2.54 (m, 2H), 2.47-2.27 (m, 2H), 1.50-1.41 (m, 2H), 0.97 (s, 9H). 13C NMR (75 MHz, CDCl3): 178.7, 151.6, 109.5, 73.4, 49.3, 32.5, 30.3, 29.9, 25.6. IR (neat): 3395, 2916, 1728, 1650, 901 cm-1. HRMS: (m/z) calcd for C11H20O3Na ([M+Na]+): 223.1310; found: 223.1296.

2: 5-hydroxy-4-methylene-6-phenylhexanoic acid

General procedure A was applied using ethyl 4-bromopent-4-enoate (4.50 mmol, 0.93 g), CrCl2 (9.60 mmol, 1.18 g), NiCl2 (0.9 mmol, 0.077 g), and 2-phenylacetaldehyde (4.00 mmol, 0.36 g). The intermediate product was hydrolyzed by using 0.5 M aqueous solution of KOH (12.0 mmol). Purification of the crude product by silica gel flash column chromatography (70% EtOAc in hexane) yielded pure 5-hydroxy-4-methylene-6-phenylhexanoic acid (0.22 g, 34% yield, yellow oil). 1H NMR (300 MHz, CDCl3): δ 7.37-7.20 (m, 5H), 5.09 (s, 1H), 4.89 (s, 1H), 4.41-4.28 (m, 1H), 2.99-2.77 (m, 2H), 2.68-2.56 (m, 2H), 2.54-2.32 (m, 2H). 13C NMR (75 MHz, CDCl3): δ 178.7, 148.9, 138.0, 126.6, 111.0, 76.3, 42.4, 32.5, 25.9. IR (neat): 3495, 2920, 1708, 1180, 1030 cm-1. HRMS (m/z) calcd for C13H16O3 :220.1099; found: 220.1092.

34: 5-hydroxy-4-methylenehexanoic acid

General procedure A was applied using ethyl 4-bromopent-4-enoate (4.50 mmol, 0.93 g), CrCl2 (9.60 mmol, 1.18 g), NiCl2 (0.9 mmol, 0.077 g), and 3,3-acetaldehyde (3.00 mmol, 0.13 g). The intermediate product was hydrolyzed by using 0.5 M aqueous solution of KOH (12.00 mmol). Purification of the crude product by silica gel flash column chromatography (15% isopropanol in hexane) yielded pure 5-hydroxy-4-methylenehexanoic acid (0.12 g, 27% yield over two steps, pale yellow oil). The compound undergoes fast self-condensation at room temperature. 1H NMR (300 MHz, CDCl3): δ 7.08-6.33 (broad s, 1H), 5.08 (s, 1H), 4.82 (s, 1H), 4.36-4.21 (m, 1H), 2.66-2.49 (m, 2H), 2.48-2.27 (m, 2H), 1.34-1.24 (m, 3H). 13C NMR (75 MHz, CDCl3) δ 178.6, 150.9, 109.4, 71.1, 32.5, 25.8, 21.9. IR (neat): 3420, 3975, 1707, 1651, 902 cm-1. HRMS: (m/z) calcd for C7H12O3Na ([M+Na]+): 167.0679; found: 167.0669.

47: 7-hydroxy-7-methyl-4-methyleneoct-5-enoic acid

General procedure A was applied using ethyl 4-bromopent-4-enoate (6.00 mmol, 1.24 g), CrCl2 (12.80 mmol, 1.57 g), NiCl2 (0.80 mmol, 0.10 g), and 3-methylbut-2-enal (4.00 mmol, 0.344 mL). The intermediate product was hydrolyzed by using 0.5 M aqueous solution of KOH (12.00 mmol). Purification of the crude product by silica gel flash column chromatography (10% isopropanol in hexane) yielded pure 7-hydroxy-7-methyl-4-methyleneoct-5-enoic acid (0.26 g, 35% yield over two steps, yellow oil). The product derives from acid-catalyzed alcohol migration. 1H NMR (300 MHz, CDCl3): δ 6.28-6.16 (broad m, 1H), 6.23 (d, J=16.2 Hz, 1H), 5.83 (d, J=16.2 Hz, 1H), 5.09-4.92 (m, 2H), 2.59-2.46 (m, 4H), 1.34 (s, 6H).13C NMR (75 MHz, CDCl3): δ 178.5, 143.6, 136.8, 128.0, 115.7, 71.1, 32.7, 29.6, 26.8. IR (neat): 3391, 2972, 1708, 1609, 1364, 1148 cm-1. HRMS: (m/z) calcd for C10H16O3Na ([M+Na]+): 207.0992; found: 207.0991.

Intramolecular Tsuji-Trost Cyclization:

General Procedure C: To an oven-dried flask was added hydroxy carboxylic acid (1.0 equiv), NaOAc (2.0 equiv), and Pd(PPh3)4 (0.5 equiv). The flask was evacuated and filled with nitrogen. Toluene (0.1 M) was added and solution stirred in a pre-heated oil bath at 100-C for 6 h. The solvent was removed under vacuum, and the crude product was purified by silica gel flash column chromatography.

13: 5-benzylidenetetrahydro-2H-pyran-2-one

General procedure C was applied using 4-(hydroxy(phenyl)methyl)pent-4-enoic acid 11 (0.5 mmol, 0.103 g), NaOAc (1.0 mmol, 0.082 g), and Pd(PPh3)4 (0.025 mmol, 0.029 g). Purification of the crude product by silica gel flash column chromatography (30% EtOAc in hexane) yielded pure 5-benzylidenetetrahydro-2H-pyran-2-one (0.088 g, 93% yield, ratio 84:16, white solid). M.p. 90-92° C. 1H NMR (300 MHz, CDCl₃, mixture of E and Z isomers): δ 7.42-7.06 (m, 10H), 6.57 (s, 1H, minor), 6.52 (s, 1H, major), 5.09 (s, 2H, minor), 4.88 (s, 2H, major), 2.97-2.84 (m, 4H), 2.82-2.62 (m, 4H). 13C NMR (75 MHz, CDCl3): major diastereoisomer: δ 172.7, 128.6, 128.5, 127.5, 127.4, 73.3, 29.2, 23.7; minor diastereoisomer, characteristic signals: δ 135.8, 130.6, 68.1, 30.2, 27.6. IR (neat): 2925, 1740, 1730, 1600, 1598, 1438, 1371, 1329, 1241, 1180, 1134, 1030, 967, 913 cm-1. HRMS (m/z) calcd for C12H12O2Na ([M+Na]+): 211.0728; found: 211.0729.

15:5-(naphthalen-2-ylmethylene)tetrahydro-2H-pyran-2-one

General procedure B was applied using 4-(hydroxy(naphthalen-2-yl)methyl)pent-4-enoic acid Substrate a (0.5 mmol, 0.128 g), NaOAc (1.0 mmol, 0.082 g), and Pd(PPh3)4 (0.025 mmol, 0.029 g). Purification of the crude product by silica gel flash column chromatography (10% to 70% diethyl ether in hexane) yielded pure 5-(naphthalen-2-ylmethylene) tetrahydro-2H-pyran-2-one (0.086 g, 72% yield, ratio 83:17, pale yellow solid). M.p. 136-140-C. 1H NMR (300 MHz, CDCl3, mixture of E and Z isomers): δ 7.88-7.72 (m, 8H), 7.53-7.38 (m, 6H), 6.73-6.63 (m, 2H), 5.18 (s, 2H, minor diastereoisomer), 4.93 (s, 2H, major diastereomer), 3.02 (t, j=8.1 Hz, 4H), 2.79-2.69 (m, 4H). 13C NMR (75 MHz, CDCl3) major diastereoisomer: δ 172.8, 135.0, 133.4, 132.5, 130.9, 128.1, 128.0, 127.8, 127.6, 127.5, 126.5, 126.5, 126.4, 73.4, 29.3, 23.9; minor diastereoisomer, characteristic peaks: 68.2, 30.3, 27.8. IR (neat): 2922, 1732, 1259, 1030 cm-1. HRMS (m/z) calcd for C16H14O2 ([M+H]+): 239.1072; found: 239.1066.

16:4-((6-oxodihydro-2H-pyran-3(4H)-ylidene) methyl)benzaldehyde

General procedure C was applied using 4-((4-formylphenyl)(hydroxy)methyl)pent-4-enoic acid Substrate b (0.5 mmol, 0.117 g), NaOAc (1.0 mmol, 0.082 g), and Pd(PPh3)4 (0.025 mmol, 0.029 g). Purification of the crude product by silica gel flash column chromatography (40% EtOAc in hexane) yielded pure 4-((6-oxodihydro-2H-pyran- 3(4H)-ylidene)methyl)benzaldehyde (0.022 g, 20% yield, ratio 78:22, pale yellow solid). M.p. 61-63° C. 1H NMR (300 MHz, CDCl$_3$, mixture of E and Z isomers): δ 10.00 (s, 2H), 7.93-7.81 (m, 4H), 7.52-7.42 (m, 2H, major), 7.31-7.17 (m, 2H, minor), 6.65-6.53 (m, 2H), 5.09 (s, 2H, minor), 4.91 (s, 2H, major), 3.01-2.80 (m, 4H), 2.72 (t, j=7.1 Hz, 4H). 13C NMR (75 MHz, CDCl$_3$): major diastereoisomer: δ 191.6, 172.2, 141.9, 135.1, 134.1, 129.9, 129.2, 126.4, 73.1, 29.0, 24.0; minor diastereoisomer, characteristic peaks: 67.8, 30.2, 27.7. IR (neat): 2850, 1736, 1697, 1597, 1563, 1165, 814 cm-1. HRMS (m/z) calcd for C13H12O3Na ([M+Na]+): 239.0679; found: 239.0674.

17:
5-(3-methoxybenzylidene)tetrahydro-2H-pyran-2-one

General procedure C was applied using 4-(hydroxy(2-methoxyphenyl)methyl)pent-4-enoic acid Substrate c(0.5 mmol, 0.118 g), NaOAc (1.0 mmol, 0.083 g), and Pd(PPh3)4 (0.025 mmol, 0.029 g). Purification of the crude product by silica gel flash column chromatography (30% EtOAc in hexane) yielded pure 5-(3-methoxybenzylidene) tetrahydro-2Hpyran-2-one (0.077 g, 71% yield, ratio 69:31, pale yellow wax). 1H NMR (300 MHz, CDCl3, mixture of E and Z isomers): δ 7.32-7.16 (m, 4H) 6.98-6.84 (m, 4H), 6.68 (s, 1H, major), 6.60 (s, 1H, minor), 4.95 (s, 2H, minor), 4.89 (s, 2H, major), 3.82 (s, 6H), 2.82-2.70 (m, 4H), 2.70-2.58 (m, 4H). 13C NMR (75 MHz, CDCl3): major diastereoisomer: δ 172.7, 156.9, 130.6, 129.1, 128.9, 124.6, 122.5, 120.2, 110.6, 73.4, 55.4, 29.5, 23.4; minor diastereoisomer, characteristic signals: δ 156.7, 129.8, 123.4, 68.5, 55.3, 30.2, 27.4. IR (neat): 2959, 1733, 1597, 1242, 1024 cm-1. HRMS (n/z) calcd for C13H14O3Na ([M+Na]+): 241.0835; found: 241.0835.

18:
5-(4-fluorobenzylidene)tetrahydro-2H-pyran-2-one

General procedure C was applied using 4-((4-fluorophenyl)(hydroxy)methyl)pent-4-enoic acid Substrate d (0.5 mmol, 0.112 g), NaOAc (1.0 mmol, 0.082 g), and Pd(PPh3)4 (0.025 mmol, 0.029 g). Purification of the crude product by silica gel flash column chromatography (30% EtOAc in hexane) yielded pure 5-(4-fluorobenzylidene) tetrahydro-2H-pyran-2-one (0.063 g, 61% yield, ratio 76:24, gummy liquid). 1H NMR (300 MHz, CDCl3, mixture of E and Z isomers): δ 7.29-7.24 and 7.08-7.02 (m, 8H), 6.52 (s, 1H, minor), 6.48 (s, 1H, major), 5.04 (s, 2H, minor), 4.85 (s, 2H, major), 2.90-2.84 (t, j=7.1 Hz, 4H), 2.78-2.67 (m, 8H). 13C NMR (75 MHz, CDCl3): major diastereoisomer: δ 172.6, 161.8 (d, 1J(F-C)=246.8 Hz), 130.4, 130.3 (d, J(F-C)=1.5 Hz), 130.1 (d, J(F-C)=8.3 Hz), 126.3, 115.5 (d, J(F-C)=21.0 Hz), 73.2, 29.1, 23.6; minor diastereoisomer, characteristic signals: δ 172.1, 131.9 (d, J(F-C)=3.8 Hz), 126.4, 67.9, 30.2, 27.5. 19F NMR (282 MHz, CDCl3): −62.79 and −62.84. IR (neat): 2926, 1737, 1601, 1507, 1439, 1258, 1221, 1200, 1175, 1150, 1050, 900, 875, 828 cm-1. HRMS (m/z) calcd for C12H11FO2Na ([M+Na]+): 229.0635; found: 229.0638.

19:5-(4-(benzyloxy)-3-methoxybenzylidene)tetrahydro-2H-pyran-2-one

General procedure B was applied using 4-((4-(benzyloxy)-3-methoxyphenyl)(hydroxy)methyl)pent-4-enoic acid Substrate e (0.5 mmol, 0.171 g), NaOAc (1.0 mmol, 0.082 g), and Pd(PPh3)4 (0.025 mmol, 0.029 g). Purification of the crude product by silica gel flash column chromatography (40% EtOAc in hexane) yielded pure 5-(4-(benzyloxy)-3-methoxybenzylidene)tetrahydro-2H-pyran-2-one (0.110 g, 68% yield, ratio 84:16, pale yellow solid). M.p. 107-111° C. 1H NMR (300 MHz, CDCl$_3$, mixture of E and Z isomers): δ 7.51-7.23 (m, 10H), 6.90-6.75 (m, 6H), 6.52-6.37 (m, 2H), 5.16 (s, 4H), 5.08 (s, 2H, minor diastereomer), 4.83 (s, 2H, major diastereomer), 3.88 (s, 6H), 2.96-2.61 (in, 8H). 13C NMR (75 MHz, CDCl3) major diastereomer: δ 172.9, 149.3, 147.7, 136.9, 129.3, 128.9, 128.6, 127.9, 127.2, 121.4, 113.7, 112.6, 73.5, 70.9, 56.0, 29.3, 23.8; minor diastereomer, characteristic peaks: δ 121.2, 112.3, 68.3, 30.4, 27.6. IR (neat): 2914, 1741, 1602, 1582, 1252, 1012 cm-1. HRMS (m/z) calcd for C$_{20}$H2004Na ([M+Na]+): 347.1259; found: 347.1253.

20: 5-(thiophen-2-ylmethylene)tetrahydro-2H-pyran-2-one

General procedure C was applied using 4-(hydroxy(thiophen-2-yl)methyl)pent-4-enoic acid Substrate f (0.5 mmol, 0.110 g), NaOAc (1.0 mmol, 0.082 g), and Pd(PPh3)4 (0.025 mmol, 0.029 g). Purification of the crude product by silica gel flash column chromatography (10% EtOAc to 20% in hexane) yielded pure 5-(thiophen-2-ylmethylene)tetrahydro-2H-pyran-2-one (0.057 g, 59% yield, ratio 91:9, pale yellow solid). M.p. 123-125° C. 1H NMR (300 MHz, CDCl3, mixture of E and Z isomers): δ 7.42-7.25 (m, 1H), 7.14-7.03 (m, 2H), 6.83-6.64 (m, 1H), 4.87 (s, 2H), 2.94-2.84 (m, 2H), 2.84-2.71 (m, 2H). 13C NMR (75 MHz, CDCl3) δ 172.8, 139.3, 128.2, 128.0, 127.2, 126.6, 120.8, 72.9, 28.9, 24.3. IR (neat): 3098, 2916, 1701, 1644, 1250, 1132, 1020, 702 cm-1. HRMS (m/z) calcd for C10H10O2SNa ([M+Na]+): 217.0299; found: 217.0287.

21:
5-(4-vinylbenzylidene)tetrahydro-2H-pyran-2-one

General procedure C was applied using 4-(hydroxy(4-vinylphenyl)methyl)pent-4-enoic acid Substrate g (0.5 mmol, 0.116 g), NaOAc (1.0 mmol, 0.082 g), and Pd(PPh3)4 (0.025 mmol, 0.029 g). Purification of the crude product by silica gel flash column chromatography (20% EtOAc in hexane) yielded pure 5-(4-vinylbenzylidene)tetrahydro-2H-pyran-2-one (0.071 g, 67% yield, ratio 77:23, white solid). M.p. 119-122° C. 1H NMR (300 MHz, CDCl3, mixture of E and Z isomers): δ 7.51-7.36 (m, 4H), 7.36-7.20 (m, 2H, major), 7.20-7.00 (m, 2H, minor), 6.83-6.65 (m, 2H), 6.58-6.52 (m, 1H, minor), 6.52-6.44 (m, 1H, major), 5.78 (d, J=17.7 Hz, 2H), 5.28 (d, J=10.8 Hz, 2H), 5.11 (s, 1H, minor), 4.88 (s, 1H, major), 2.99-2.66 (m, 8H). 13C NMR (75 MHz, CDCl3): major diastereoisomer: δ 172.7, 136.2, 130.6, 128.9, 128.7, 127.1, 126.3, 114.4, 73.5, 29.2, 23.9; minor diastereoisomer, characteristic peaks: δ 136.8, 68.2, 30.4, 27.8. IR (neat): 2890, 1736, 1395, 1256, 1130, 884 cm-1. HRMS (m/z) calcd for C14H14O2Na ([M+Na]+): 237.0891; found: 237.0887.

22: tert-butyl 2-(5-benzylidene-2-oxotetrahydro-2H-pyran-3-yl)acetate

General procedure C was applied using 2-(2-(tert-butoxy)-2-oxoethyl)-4-(hydroxy(phenyl)methyl)pent-4-enoic acid Substrate h (0.5 mmol, 0.160 g), NaOAc (1.0 mmol, 0.082 g), and Pd(PPh3)4 (0.025 mmol, 0.029 g). Purification of the crude product by silica gel flash column chromatography (20% EtOAc in hexane) yielded pure tert-butyl 2-(5- benzylidene-2-oxotetrahydro-2H-pyran-3-yl)acetate as separable diastereoisomers (0.127 g, 84% yield, ratio 79:21). E isomer (yellow solid): M.p. 83-88° C. 1H NMR (300 MHz, CDCl3): δ 7.44-7.20 (m, 5H), 6.55-6.42 (m, 1H), 5.07-4.97 (m, 1H), 4.84-4.59 (m, 1H) 3.23-3.07 (m, 2H), 2.89-2.73 (m, 1H), 2.63-2.45 (m, 1H), 2.45-2.31 (m, 1H), 1.45 (s, 9H). 13C NMR (75 MHz, CDCl3): δ 173.8, 170.7, 135.8, 130.5, 128.6, 128.5, 127.6, 127.4, 123.5, 81.2, 73.0, 36.2, 35.8, 30.1, 28.0. IR (neat): 2924, 2854, 1732, 1365, 1120 cm-1. HRMS (m/z) calcd for C18H22O4Na ([M+Na]+): 325.1410; found: 325.1412. Z isomer (white solid): M.p. 107-111° C. 1H NMR (300 MHz, CDCl3): δ 7.43-7.23 (m, 3H), 7.17-7.03 (m, 2H), 6.60-6.50 (m, 1H), 5.18-4.96 (m, 2H), 3.30-3.09 (m, 1H), 3.02-2.76 (m, 2H), 2.64-2.48 (m, 1H), 2.48-2.31 (m, 1H), 1.47 (s, 9H). 13C NMR (75 MHz, CDCl3): δ 173.7, 170.7, 135.6, 130.7, 128.5, 127.7, 127.4, 81.2, 67.8, 36.6, 36.1, 33.3, 28.1. IR (neat): 2979, 2928, 1732, 1375, 1138 cm-1. HRMS (m/z) calcd for C18H22O4Na ([M+Na]+): 325.1410; found: 325.1413.

23: 5-benzylidene-3-(2-methyl-1,3-dioxolan-2-yl)tetrahydro-2H-pyran-2-one

General procedure C was applied using 4-(hydroxy(phenyl)methyl)-2-(2-methyl-1,3-dioxolan-2-yl)pent-4-enoic acid Substrate i (0.5 mmol, 0.146 g), NaOAc (1.0 mmol, 0.082 g), and Pd(PPh3)4 (0.025 mmol, 0.029 g). Purification of the crude product by silica gel flash column chromatography (30% EtOAc in hexane) yielded pure 5-benzylidene-3-(2-methyl-1,3-dioxolan-2-yl)tetrahydro-2H-pyran-2-one as separable E and Z isomers (0.081 g, 68% yield, ratio 60:40). E isomer (pale yellow solid): M.p. 89-93° C. 1H NMR (300 MHz, CDCl3): δ 7.43-7.24 (m, 5H), 6.52-6.45 (s, 1H), 5.00-4.88 (m, 1H), 4.87-4.75 (m, 1H), 4.08-3.92 (m, 4H), 3.26-3.12 (m, 1H), 3.04-2.92 (m, 1H), 2.81-2.67 (m, 1H), 1.57-1.50 (s, 3H). 13C NMR (75 MHz, CDCl3): δ 171.0, 135.9, 130.5, 128.7, 128.5, 127.5, 126.9, 108.9, 72.9, 64.9, 47.4, 25.8, 21.8. IR (neat): 2928, 2886, 1739, 1370, 1034 cm-1. HRMS (m/z) calcd for C16H18O4 ([M+H]+): 275.1283; found: 275.1275. Z isomer (yellow wax): 1H NMR (300 MHz, CDCl3): δ 7.40-7.32 (m, 2H), 7.30-7.27 (m, 1H), 7.12-7.05 (m, 2H), 6.54-6.45 (m, 1H), 5.26-5.17 (m, 1H), 5.05-4.98 (m, 1H), 4.07-3.92 (m, 4H), 3.03-2.95 (m, 2H), 2.86-2.70 (m, 1H), 1.54 (s, 3H). 13C NMR (75 MHz, CDCl3): δ 170.9, 135.8, 131.0, 128.5, 127.2, 126.4, 109.9, 68.5, 65.2, 64.9, 48.6, 29.6, 22.4. IR (neat): 2978, 2890, 1736, 1034 cm-1. HRMS (m/z) calcd for C16H18O4Na ([M+Na]+): 297.1181; found: 297.1094.

24: 3-allyl-5-benzylidenetetrahydro-2H-pyran-2-one

General procedure C was applied using 2-allyl-4-(hydroxy(phenyl)methyl)pent-4-enoic acid Substrate j (0.45 mmol, 0.110 g), NaOAc (0.97 mmol, 0.080 g), and Pd(PPh3)4 (0.022 mmol, 0.026 g). Purification of the crude product by silica gel flash column chromatography (30% diethyl ether in hexane) yielded pure tert-butyl 3-allyl-5-benzylidenetetrahydro-2H-pyran-2-one as a mixture of diastereoisomers (0.063 g, 61% yield, ratio 70:30, yellow solid). 1H NMR (300 MHz, CDCl3, mixture of E and Z isomers): δ 7.53-7.02 (m, 5H), 6.60-6.44 (m, 1H), 5.97-5.74 (m, 1H) 5.25-5.04 (m, 2H), 5.04-4.94 (m, 1H), 4.77-4.66 (m, 1H), 3.20-2.84 (m, 1H), 2.82-2.60 (m, 2H), 2.60-2.40 (m, 1H), 2.40-2.16 (m, 1H). 13C NMR (75 MHz, CDCl$_3$): major diastereoisomer: δ 174.3, 145.9, 134.8, 128.7, 128.5, 127.5, 127.2, 117.7, 72.8, 38.5, 34.4, 29.8; minor diastereoisomer, characteristic peaks: 135.9, 130.8, 67.9, 39.4, 32.9. IR (neat): 2896, 1732, 1641, 1165 cm-1. HRMS (m/z) calcd for C15H16O2Na ([M+Na]+): 251.1048; found: 251.1044.

30: 5-benzylideneoxepan-2-one

General procedure C was applied using 5-(hydroxy(phenyl)methyl)hex-5-enoic acid 27 (0.5 mmol, 0.110 g), NaOAc (1.0 mmol, 0.082 g), and Pd(PPh3)4 (0.025 mmol, 0.029 g). Toluene (0.1 M, 5 mL) was added and the solution was stirred in a pre-heated oil bath at 100-C for 21 h. Purification of the crude product by silica gel flash column chromatography (10% EtOAc in hexane) yielded as a mixture of E and Z isomers of 5-benzylideneoxepan-2-one (0.015 g, 15% yield, ratio 52:47, white solid). M.p. 118-1230° C. 1H NMR (300 MHz, CDCl3, mixture of E and Z isomers): 67.45-7.11 (m, 10H), 6.67-6.56 (m, 2H), 4.86-4.76 (m, 2H, minor isomer), 4.76-4.61 (m, 2H, major isomer), 2.58-2.26 (m 8H), 2.06-1.76 (m. 4H). 13C NMR (75 MHz, CDCl3, mixture of E and Z isomers): δ 173.09, 172.75, 136.46, 135.89, 130.77, 130.34, 128.74, 128.35, 127.09, 69.20, 62.45, 35.12, 34.64, 27.80, 24.24, 23.57. IR (neat): 2926, 1724, 1445, 1239, 1139 cm-1. HRMS (m/z) calcd for C13H14O2Na ([M+Na]+): 225.0886 found: 225.0886.

31: 5-benzylideneoxocan-2-one

General procedure C was applied using 6-(hydroxy(phenyl)methyl)hept-6-enoic acid 28 (0.5 mmol, 0.117 g), NaOAc (1.0 mmol, 0.082 g), and Pd(PPh3)4 (0.025 mmol, 0.029 g). Toluene (0.1 M, 5 mL) was added and the solution was stirred in a pre-heated oil bath at 100-C for 24 h. The solvent was removed under vacuum, and the crude product was purified by silica gel flash column chromatography (15% EtOAc in hexane) yielding a mixture of E and Z isomers of 5-benzylideneoxocan-2-one (0.016 g, 14% yield, ratio 69:31, white wax). 1H NMR (300 MHz, CDCl3, mixture of E and Z isomers): δ 7.46-7.11 (m, 10H), 6.64-6.54 (m, 2H), 4.81-4.71 (m, 2H, minor diastereoisomer), 4.70-4.61 (m, 2H, major diastereoisomer), 2.48-2.22 (m, 8H), 1.85-1.64 (m, 4H), 1.64-1.46 (m, 4H). 13C NMR (75 MHz, CDCl3): major stereoisomers: δ 173.21, 136.89, 130.62, 128.70, 128.27, 127.00, 69.24, 36.35, 34.12, 28.66, 27.16, 25.33; major stereoisomers, characteristic peaks: 173.38, 136.54, 62.42, 34.38, 28.01, 27.16. IR (neat): 2927, 1728, 1458, 1235, 1133 cm-1. HRMS (n/z) calcd for C14H16O2 ([M+H]+): 217.1229 found: 217.1220.

35: (E)-5-(3,3-dimethylbut-1-en-1-yl)-5-methyldihydrofuran-2(3H)-one

General procedure C was applied using 5-hydroxy-7,7-dimethyl-4-methyleneoctanoic acid 32 (0.5 mmol, 0.100 g), NaOAc (1.0 mmol, 0.082 g), and Pd(PPh3)4 (0.025 mmol, 0.029 g). Purification of the crude product by silica gel flash column chromatography (10% EtOAc in hexane) yielded pure 5-(3,3-dimethylbut-1-en-1-yl)-5-methyldihydrofuran-2(3H)-one (0.061 g, 69% yield, pale yellow oil). 1H NMR (300 MHz, CDCl$_3$): δ 5.71 (d, J=15.9 Hz, 1H), 5.40 (d, J=15.9 Hz, 1H), 2.60-2.48 (m, 2H), 2.22-1.99 (m, 2H), 1.48 (s, 3H), 1.00 (s, 9H). 13C NMR (75 MHz, CDCl3): δ 176.9, 140.7, 126.7, 85.6, 34.3, 32.7, 29.4, 28.9, 26.7. IR (neat): 2957, 2868, 1770 1228, 928 cm-1 HRMS (m/z) calcd for C11H18O2Na ([M+Na]+): 205.1204; found: 205.1201.

36: (E)-5-methyl-5-styryldihydrofuran-2(3H)-one

General procedure C was applied using 5-hydroxy-4-methylene-6-phenylhexanoic acid 33 (0.5 mmol, 0.110 g), NaOAc (1.0 mmol, 0.082 g), and Pd(PPh3)4 (0.025 mmol, 0.029 g). Purification of the crude product by silica gel flash column chromatography (10% EtOAc in hexane) yielded pure (E)-5-methyl-5-styryldihydrofuran-2(3H)-one (0.044 g, 44% yield, pale yellow wax). 1H NMR (300 MHz, CDCl3): δ 7.42-7.25 (m, 5H), 6.62 (d, J=16.1 Hz, 1H), 6.24 (d, J=16.1 Hz, 1H), 2.66-2.52 (m, 2H), 2.36-2.06 (m, 2H), 1.61 (s, 3H). 13C NMR (75 MHz, CDCl3): δ 176.6, 135.8, 131.1, 128.7, 128.1, 126.6, 85.4, 34.4, 28.9, 26.8. IR (neat): 2975, 2828, 1766, 1197 cm-1. HRMS (m/z) calcd for C13H14O2 ([M+H]+): 203.1067; found: 203.1074.

37: 5-methyl-5-vinyldihydrofuran-2(3H)-one (*Lavender lactone*) (S. Baskaran, Imadul Islam, S. Chandrasekaran, *J. Org. Chem.* 1990, 55, 891-895):

General procedure C was applied using 4-(hydroxy(phenyl)methyl)-2-(2-methyl-1,3-dioxolan-2-yl)pent-4-enoic acid 34 (0.5 mmol, 0.072 g), NaOAc (1.0 mmol, 0.082 g), and Pd(PPh3)4 (0.025 mmol, 0.029 g). Purification of the crude product by silica gel flash column chromatography (30% EtOAc in hexane) yielded pure 5-methyl-5-vinyldihydrofuran-2(3H)-one (0.021 g, 33% yield, yellow oil). 1H NMR (300 MHz, CDCl3): δ 5.96-5.70 (m, 1H), 5.35-6.21 (m, 1H), 5.21-5.00 (m, 1H), 2.60-2.50 (m, 2H), 2.26-2.01 (m, 2H), 1.49 (s, 3H). 13C NMR (75 MHz, CDCl3): δ 176.8, 139.9, 113.8, 85.5, 33.7, 28.6, 26.3. IR (neat): 2979, 1766, 1126, 930 cm-1.

50: (E)-5-(3-methylbut-2-en-1-ylidene)tetrahydro-2H-pyran-2-one

General procedure C was applied using 7-hydroxy-7-methyl-4-methyleneoct-5-enoic acid 47 (0.7 mmol, 0.13 g), NaOAc (1.4 mmol, 0.115 g), and Pd(PPh3)4 (0.03 mmol, 0.035 g). Purification of the crude product by silica gel flash column chromatography (20% EtOAc in hexane) yielded pure 5-(3-methylbut-2-en-1-ylidene)tetrahydro-2Hpyran-2-one (0.028 g, 24% yield, ratio 79:21, yellow oil). 1H NMR (300 MHz, CDCl$_3$): δ 6.24 (d, J=11.6 Hz, 1H), 5.83 (d, J=11.4 Hz, 1H), 4.74 (s, 2H), 2.70-2.58 (m, 4H), 1.82 (s, 3H), 1.76 (s, 3H). 13C NMR (75 MHz, CDCl$_3$): δ 173.2, 09 138.7, 126.5, 123.1, 119.6, 72.9, 29.2, 26.4, 22.0, 18.3. IR (neat): 2956, 1731, 1368, 1176 cm-1. HRMS (m/z) calcd for C10H14O2Na ([M+Na]+): 189.0886; found: 189.0885.

The invention claimed is:

1. A process for the preparation of a compound of formula (II) comprising the step of:

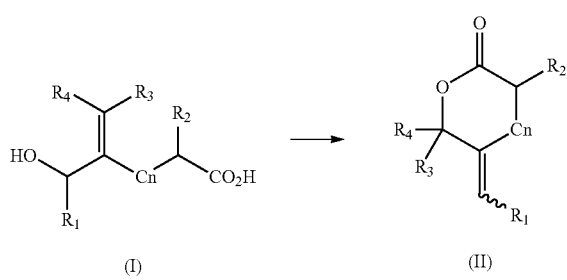

Reacting a compound of formula (I) in the presence of at least one Pd catalyst and at least one base; $R_1$ and $R_2$ are each independently selected from a group consisting of H, straight or branched $C_1$-$C_{15}$ alkyl, straight or branched $C_2$-$C_{15}$ alkenyl, straight or branched $C_2$-$C_{15}$ alkynyl, $C_5$-$C_{12}$ aryl, $C_5$-$C_{12}$ heteroaryl; $C_3$-$C_{12}$ cycloalkyl, $C_3$-$C_{12}$ heterocycloalkyl; each optionally substituted by at least one OH, amine, amide, halide, straight or branched $C_1$-$C_{15}$ alkyl, straight or branched $C_2$-$C_{15}$ alkenyl, straight or branched $C_2$-$C_{15}$ alkynyl, —O($C_1$-$C_8$ akyl), —OC(=O)($C_1$-$C_8$ alkyl), —C(=O) ($C_1$-$C_8$ alkyl), —C(=O)O($C_1$-$C_8$ alkyl); $C_5$-$C_{12}$ aryl, $C_5$-$C_{12}$ heteroaryl, $C_3$-$C_{12}$ cycloalkyl, $C_3$-$C_{12}$ heterocycloalkyl; $R_3$ and $R_4$ are H; and n is an integer being 1-6.

2. A process for the preparation of a compound of formula (IV) comprising the step of:

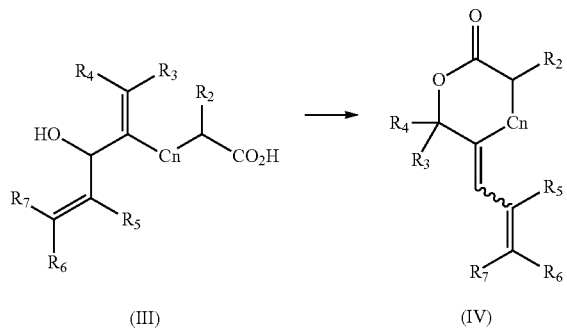

reacting a compound of formula (III) in the presence of at least one Pd catalyst and at least one base;

wherein $R_2$-$R_7$ are each independently selected from a group consisting of H, straight or branched $C_1$-$C_{15}$ alkyl, straight or branched $C_2$-$C_{15}$ alkenyl, straight or branched $C_2$-$C_{15}$ alkynyl, $C_5$-$C_{12}$ aryl, $C_5$-$C_{12}$ heteroaryl; $C_3$-$C_{12}$ cycloalkyl, $C_3$-$C_{12}$ heterocycloalkyl; each optionally substituted by at least one OH, amine, amide, halide, straight or branched $C_1$-$C_{15}$ alkyl, straight or branched $C_2$-$C_{15}$ alkenyl, straight or branched $C_2$-$C_{15}$ alkynyl, —O($C_1$-$C_8$ akyl), —OC(=O)($C_1$-$C_8$ alkyl), —C(=O)($C_1$-$C_8$ alkyl), —C(=O)O($C_1$-$C_8$ alkyl); $C_5$-$C_{12}$ aryl, $C_5$-$C_{12}$ heteroaryl, $C_3$-$C_{12}$ cycloalkyl, $C_3$-$C_{12}$ heterocycloalkyl; $R_3$ and $R_4$ are H; and n is an integer being 1-6; or $R_5$ and $R_6$ or $R_6$ and $R_7$ or $R_5$ and $R_7$ together with the two carbon atoms they are attached to form a 5 to 15 ring.

3. A process according to claim 1, wherein $R_1$ is selected from $C_5$-$C_{12}$ aryl or $C_5$-$C_{12}$ heteroaryl, optionally substituted by at least one OH, amine, amide, halide, straight or branched $C_1$-$C_{15}$ alkyl, straight or branched $C_2$-$C_{15}$ alkenyl, straight or branched $C_2$-$C_{15}$ alkynyl, —O($C_1$-$C_8$ akyl), —OC(=O)($C_1$-$C_8$ alkyl), —C(=O)($C_1$-$C_8$ alkyl), —C(=O)O($C_1$-$C_8$ alkyl); $C_5$-$C_{12}$ aryl, $C_5$-$C_{12}$ heteroaryl.

4. A process according to claim 1, wherein $R_1$ is selected from straight or branched $C_1$-$C_{15}$ alkyl, straight or branched $C_2$-$C_{15}$ alkenyl, straight or branched $C_2$-$C_5$ alkynyl, optionally substituted by at least one OH, amine, amide, halide, —O($C_1$-$C_8$ akyl), —OC(=O)($C_1$-$C_8$ alkyl), —C(=O)($C_1$-$C_8$ alkyl), —C(=O)O($C_1$-$C_8$ alkyl); $C_5$-$C_{12}$ aryl, $C_5$-$C_{12}$ heteroaryl, $C_3$-$C_{12}$ cycloalkyl, $C_3$-$C_{12}$ heterocycloalkyl.

5. A process according to claim 1, wherein $R_2$ is H.

6. A process according to claim 2, wherein $R_5$ and $R_6$ together with the two carbon atoms they are each attached to form a 5 to 15 membered ring.

7. A process according to claim 2, wherein $R_6$ and $R_7$ together with the two carbon atoms they are each attached to form a 5 to 15 membered ring.

8. A process according to claim 2, wherein $R_5$ and $R_7$ together with the two carbon atoms they are each attached to form a 5 to 15 membered ring.

9. A process according to claim 1, wherein said at least one Pd catalyst is selected from is selected from Pd(PPh$_3$)$_4$, Pd$_2$(dba)$_3$, Pd(OAc)$_2$, PdCl$_2$, Pd(acac)$_2$ and any combinations thereof.

10. A process according to claim 1, wherein said at least one base is selected from K$_2$PO$_4$, Cs$_2$CO$_3$, K$_2$CO$_3$, NaOAc and any combinations thereof.

11. A process according to claim 1, being performed in the presence of at least one organic solvent.

12. A process according to claim 1, being performed in a temperature of between 50° C. to 100° C.

13. A process for the preparation of a compound of formula (VI) comprising the step:

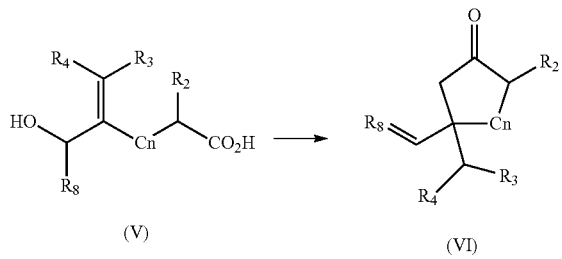

reacting a compound of formula (V) in the presence of at least one Pd catalyst and at least one base; wherein R$_2$ is selected from a group consisting of H, straight or branched C$_1$-C$_{15}$ alkyl, straight or branched C$_2$-C$_{15}$ alkenyl, straight or branched C$_2$-C$_{15}$ alkynyl, C$_5$-C$_{12}$ aryl, C$_5$-C$_{12}$ heteroaryl; C$_3$-C$_{12}$ cycloalkyl, C$_3$-C$_{12}$ heterocycloalkyl; each optionally substituted by at least one OH, amine, amide, halide, straight or branched C$_1$-C$_{15}$ alkyl, straight or branched C$_2$-C$_{15}$ alkenyl, straight or branched C$_2$-C$_{15}$ alkynyl, —O(C$_1$-C$_8$ akyl), —OC(=O)(C$_1$-C$_8$ alkyl), —C(=O)(C$_1$-C$_8$ alkyl), —C(=O)O(C$_1$-C$_8$ alkyl); C$_5$-C$_{12}$ aryl, C$_5$-C$_{12}$ heteroaryl, C$_3$-C$_{12}$ cycloalkyl, C$_3$-C$_{12}$ heterocycloalkyl; R$_3$, R$_4$ and R$_5$ are H; R$_8$ is straight or branched C$_1$-C$_{15}$ alkyl, straight or branched C$_2$-C$_{15}$ alkenyl, straight or branched C$_2$-C$_{15}$ alkynyl, each optionally substituted by at least one OH, amine, amide, halide, straight or branched C$_1$-C$_{15}$ alkyl, straight or branched C$_2$-C$_{15}$ alkenyl, straight or branched C$_2$-C$_{15}$ alkynyl, —O(C$_1$-C$_8$ akyl), —OC(=O)(C$_1$-C$_8$ alkyl), —C(=O)(C$_1$-C$_8$ alkyl), —C(=O)O(C$_1$-C$_8$ alkyl); C$_5$-C$_{12}$ aryl, C$_5$-C$_{12}$ heteroaryl, C$_3$-C$_{12}$ cycloalkyl, C$_3$-C$_{12}$ heterocycloalkyl; and n is an integer being 1-6.

14. A process according to claim 13, wherein said at least one Pd catalyst is selected from Pd(PPh$_3$)$_4$, Pd$_2$(dba)$_3$, Pd(OAc)$_2$, PdCl$_2$, Pd(acac)$_2$ and any combinations thereof.

15. A process according to claim 13, wherein said at least one base is selected from K$_2$PO$_4$, Cs$_2$CO$_3$, K$_2$CO$_3$, NaOAc and any combinations thereof.

16. A process according to claim 13, being performed in the presence of at least one organic solvent.

17. A process according to claim 13, being performed in a temperature of between 50° C. to 100° C.

* * * * *